(12) United States Patent
Katznelson et al.

(10) Patent No.: US 11,247,065 B2
(45) Date of Patent: Feb. 15, 2022

(54) MAGNETIC DEVICE FOR TREATING LIVING TISSUES

(71) Applicant: EPITECH MAG LTD., Yokneam Illit (IL)

(72) Inventors: Ehud Katznelson, Ramat Yishay (IL); Tomer Carmeli, Alonei Abba (IL); Itzik Ronen, Nirit (IL)

(73) Assignee: EPITECH MAG LTD., Yokneam Illit (IL)

( * ) Notice: Subject to any disclaimer, the term of this patent is extended or adjusted under 35 U.S.C. 154(b) by 0 days.

(21) Appl. No.: 16/634,009

(22) PCT Filed: Jul. 26, 2018

(86) PCT No.: PCT/IL2018/050831
§ 371 (c)(1),
(2) Date: Jan. 24, 2020

(87) PCT Pub. No.: WO2019/021288
PCT Pub. Date: Jan. 31, 2019

(65) Prior Publication Data
US 2020/0206524 A1   Jul. 2, 2020

(30) Foreign Application Priority Data
Jul. 26, 2017   (IL) ........................... 253677

(51) Int. Cl.
*A61N 2/02* (2006.01)
*H01F 5/04* (2006.01)
*H01F 5/06* (2006.01)
*A61N 2/00* (2006.01)

(52) U.S. Cl.
CPC ............... *A61N 2/02* (2013.01); *A61N 2/006* (2013.01); *H01F 5/04* (2013.01); *H01F 5/06* (2013.01)

(58) Field of Classification Search
None
See application file for complete search history.

(56) References Cited

U.S. PATENT DOCUMENTS

| 5,085,627 A | 2/1992 | Fedorov et al. |
| 5,135,466 A | 8/1992 | Fedorov et al. |
| 5,147,284 A | 9/1992 | Fedorov et al. |

(Continued)

FOREIGN PATENT DOCUMENTS

| CN | 203276182 | 11/2013 |
| EP | 1006892 | 6/2009 |

(Continued)

OTHER PUBLICATIONS

An International Search Report and a Written Opinion both dated Aug. 14, 2014, which issued during the prosecution of Applicant's PCT/IL2014/050401.

(Continued)

*Primary Examiner* — Christine H Matthews
(74) *Attorney, Agent, or Firm* — Sughrue Mion, PLLC

(57) ABSTRACT

A device for treating living tissue with a magnetic field. The device includes one or more coil applicators; and a generator configured to drive a stimulation coil that is housed within the coil applicator that faces a tissue being treated. The device provides a magnetic field in a range of 0.1 T to 3 T at a distance of 1 cm or less from the face of the coil applicator.

16 Claims, 20 Drawing Sheets

(56) References Cited

U.S. PATENT DOCUMENTS

| | | | |
|---|---|---|---|
| 5,725,471 | A | 3/1998 | Davey et al. |
| 5,830,139 | A | 11/1998 | Abreu |
| 7,335,156 | B2 | 2/2008 | Pattern et al. |
| 9,427,224 | B1 | 8/2016 | Jeyanandarajan |
| 10,058,710 | B2 | 8/2018 | Sher-Rosenthal et al. |
| 2001/0031906 | A1* | 10/2001 | Ishikawa ................ A61N 2/02 600/13 |
| 2002/0035358 | A1 | 3/2002 | Wang |
| 2004/0138516 | A1 | 7/2004 | Osorio et al. |
| 2005/0261542 | A1 | 11/2005 | Riehl |
| 2006/0094924 | A1 | 5/2006 | Riehl |
| 2007/0073096 | A1 | 3/2007 | Alvarado |
| 2008/0004484 | A1 | 1/2008 | Wieraszko et al. |
| 2008/0275289 | A1 | 11/2008 | Olree et al. |
| 2009/0182312 | A1 | 7/2009 | Gertner et al. |
| 2009/0216068 | A1 | 8/2009 | Thomas et al. |
| 2010/0130945 | A1 | 5/2010 | Laniado et al. |
| 2010/0239067 | A1 | 9/2010 | Gertner et al. |
| 2010/0249488 | A1 | 9/2010 | Kardos et al. |
| 2010/0298624 | A1 | 11/2010 | Becker |
| 2010/0324642 | A1 | 12/2010 | Pettinelli |
| 2011/0021863 | A1 | 1/2011 | Burnett et al. |
| 2011/0112427 | A1 | 5/2011 | Phillips et al. |
| 2012/0130398 | A1 | 5/2012 | Ackermann et al. |
| 2013/0123764 | A1 | 5/2013 | Zarsky et al. |
| 2013/0137918 | A1 | 5/2013 | Phillips et al. |
| 2013/0278898 | A1 | 10/2013 | Kato |
| 2014/0220509 | A1 | 8/2014 | Vladila |
| 2014/0257433 | A1 | 9/2014 | Ackermann et al. |
| 2014/0275718 | A1 | 9/2014 | Huang et al. |
| 2014/0316310 | A1 | 10/2014 | Ackermann et al. |
| 2014/0343349 | A1 | 11/2014 | Borsody |
| 2015/0025297 | A1 | 1/2015 | Pan et al. |
| 2015/0085249 | A1 | 3/2015 | Abreu |
| 2015/0100001 | A1 | 4/2015 | Bujak |
| 2015/0238357 | A1* | 8/2015 | Goldberg ................ A61N 2/06 600/431 |
| 2015/0328477 | A1 | 11/2015 | Gale et al. |
| 2016/0008620 | A1 | 1/2016 | Stubbeman |
| 2016/0015995 | A1 | 1/2016 | Leung et al. |
| 2016/0022992 | A1 | 1/2016 | Franke et al. |
| 2016/0067086 | A1 | 3/2016 | Tedford et al. |
| 2016/0106996 | A1 | 4/2016 | Sher-Rosenthal et al. |
| 2016/0158562 | A1 | 6/2016 | Bornzin et al. |
| 2016/0367806 | A1 | 12/2016 | Kahook |
| 2017/0131765 | A1 | 5/2017 | Perek et al. |
| 2017/0333249 | A1 | 11/2017 | Herchman, Jr. et al. |
| 2017/0354818 | A1 | 12/2017 | De Toni et al. |
| 2018/0161579 | A1 | 6/2018 | Franke et al. |
| 2018/0256906 | A1 | 9/2018 | Pivonka et al. |
| 2019/0046810 | A1 | 2/2019 | Carmeli et al. |
| 2019/0344076 | A1 | 11/2019 | Irazoqui et al. |

FOREIGN PATENT DOCUMENTS

| | | |
|---|---|---|
| GB | 2271931 | 5/1994 |
| JP | 2005334586 | 12/2005 |
| KR | 101134657 | 4/2012 |
| KR | 20180004669 | 1/2018 |
| RU | 2260404 | 9/2005 |
| RU | 2368405 | 9/2009 |
| RU | 2010138239 | 3/2012 |
| RU | 2011114847 | 10/2012 |
| RU | 2499614 | 11/2013 |
| RU | 2581495 | 4/2016 |
| SU | 1076126 | 4/1982 |
| WO | 9919020 | 4/1999 |
| WO | 0178829 | 10/2001 |
| WO | 2005/105013 | 11/2005 |
| WO | 2006/107951 | 10/2006 |
| WO | 2009011529 | 1/2009 |
| WO | 2013/073840 | 5/2013 |
| WO | 2014/181327 | 11/2014 |
| WO | 2015/034154 | 3/2015 |
| WO | 2017/081087 | 5/2017 |
| WO | 2017/125909 | 7/2017 |
| WO | 2017/208168 | 12/2017 |
| WO | 2018/018724 | 2/2018 |
| WO | 2019/021288 | 1/2019 |

OTHER PUBLICATIONS

An International Preliminary Report on Patentability dated Nov. 10, 2015, which issued during the prosecution of Applicant's PCT/IL2014/050401.

An Office Action dated Apr. 19, 2018, which issued during the prosecution of U.S. Appl. No. 14/888,756.

An Office Action dated Sep. 28, 2017, which issued during the prosecution of U.S. Appl. No. 14/888,756.

Notice of Allowance dated Jul. 17, 2018, which issued during the prosecution of U.S. Appl. No. 14/888,756.

An Office Action dated Oct. 6, 2020, which issued during the prosecution of U.S. Appl. No. 16/039,659.

An Advisory Action dated May 14, 2018, which issued during the prosecution of U.S. Appl. No. 14/888,756.

An Office Action dated May 13, 2020, which issued during the prosecution of U.S. Appl. No. 16/039,659.

An English Translation of an Office Action dated Jan. 19, 2021, which issued during the prosecution of Chinese Patent Application No. 201680081997.5.

An English Translation of an Office Action dated Apr. 16, 2020, which issued during the prosecution of Chinese Patent Application No. 201680081997.5.

European Search Report dated Aug. 2, 2019, which issued during the prosecution of Applicant's European App No. 16886201.9.

The Magstim Company Ltd., "Magstim®Rapid2P/N 3576-23-09 Operating Manual", Nov. 2009, 61 pages.

Koller, Loszlo, and Balazs Novak. "Ridged surface for reducing eddy-current losses in ferromagnetic shielding." Electrical Engineering 91.3 (2009): 117.

Yamada, H., and M. Nanba. "Eddy current loss in grooved solid poles." IEEE Transactions on Magnetics 14.5 (1978): 380-382.

Lopez-Boado et al., "Macrolides as immunomodulatory medications for the therapy of chronic lung disease", Current Opinion in Pharmacology, 2008, www.sciencedirect.com, pp. 286-291.

Okano et al., "Biphasic Effects of Static Magnetic Fields on Cutaneous Microcirculation in Rabbits", Bioelectromagnetics 20, 1999, pp. 161-171.

MacCabee et al., "Stimulation of the Human Nervous System Using the Magnetic Coil", Journal of Clinical Neurophysiology, vol. 8, No. 1, 1991, pp. 38-55.

Wang et al., "Reduced Innervation and Delayed Re-Innervation After Epithelial Wounding in Type 2 Diabetic Goto-Kakizaki Rats", The American Journal of Pathology, vol. 181, No. 6, Dec. 2012, pp. 2058-2066.

Yang et al., "Substance P Promotes Diabetic Corneal Epithelial Wound Healing Through Molecular Mechanisms Mediated via the Neurokinin-1 Receptor", Diabetes, vol. 63, Dec. 2014, pp. 4262-4274.

Beuerman et al., "Sensory Denervation of the Rabbit Cornea Affects Epithelial Properties", Experimental Neurology, 39, 1980, pp. 196-201.

Nagano et al., "Effects of Substance P and IGF-1 in Corneal Epithelial Barrier Function and Wound Healing in a Rat model of Neurotrophic Keratopathy", Investigative Opthalmology & Visual Science, Sep. 2003, vol. 44, No. 9, pp. 3810-3815.

Dswald et al., "Communication between Corneal Epithelial Cells and Trigeminal Neurons is Facilitated by Purinergic (P2) and Glutamatergic Receptors", PLOS ONE, Sep. 2012, vol. 7, Issue 9, 15 pages.

Toshida et al., "Evaluation of Novel Dry Eye Model: Preganglionic Parasympathetic Denervation in Rabbit", Investigative Opthalmology & Visual Science, Oct. 2007, vol. 48, No. 10, pp. 4468-4475.

Araki-Sasaki et al., "Substance P-lnduced Cadherin Expression and Its Signal Transduction in a Cloned Human Corneal Epithelial Cell Line", Journal of Cellular Physiology, 2000, pp. 189-195.

(56) References Cited

OTHER PUBLICATIONS

Reid et al., "Stimulation of Epithelial Cell Growth by the Neuropeptide Substance P", Journal of Cellular Biochemistry, 52, 1993, pp. 476-485.
Garcia-Hirschfeld et al., "Neurotrophic Influences on Corneal Epithelial Cells", Exp. Eye Res., 1994, 59, pp. 597-605.
Yamada et al., "Functional genomics and depression research Beyond the monoamine hypothesis", European Neuropsychopharmacology, 12, 2002, pp. 235-244.
An International Search Report and a Written Opinion both dated Jul. 14, 2021, which issued during the prosecution of Applicant's PCT/IL2021/050035.

* cited by examiner

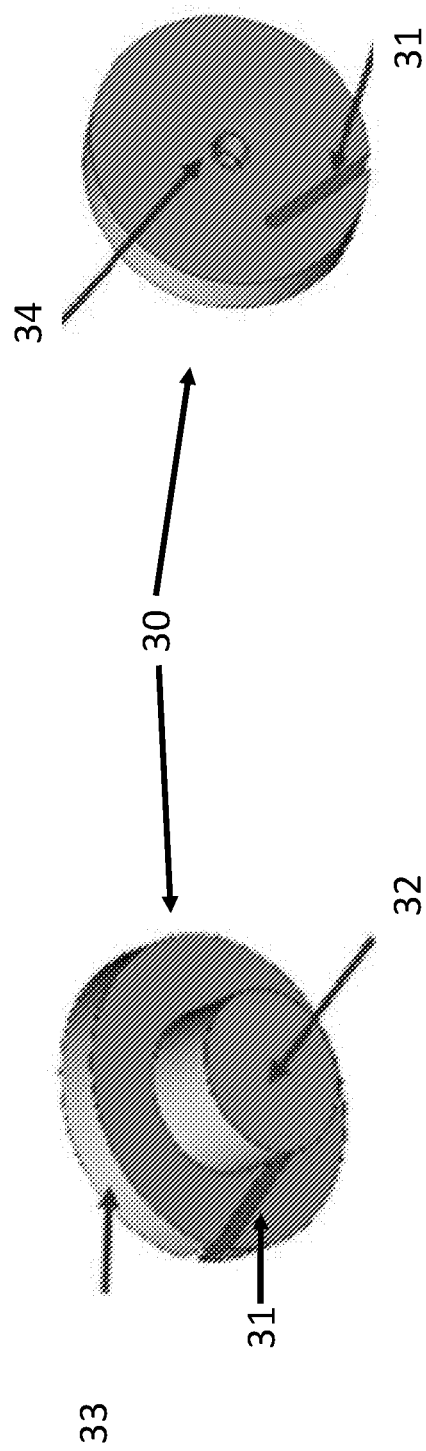

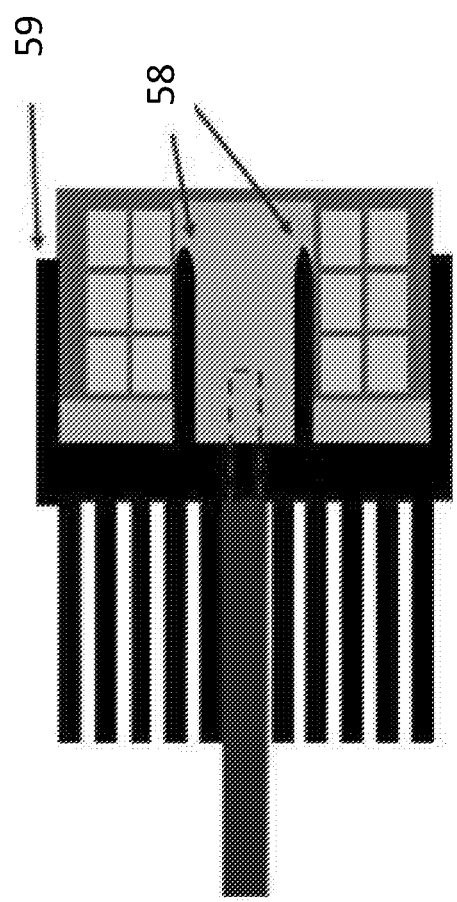

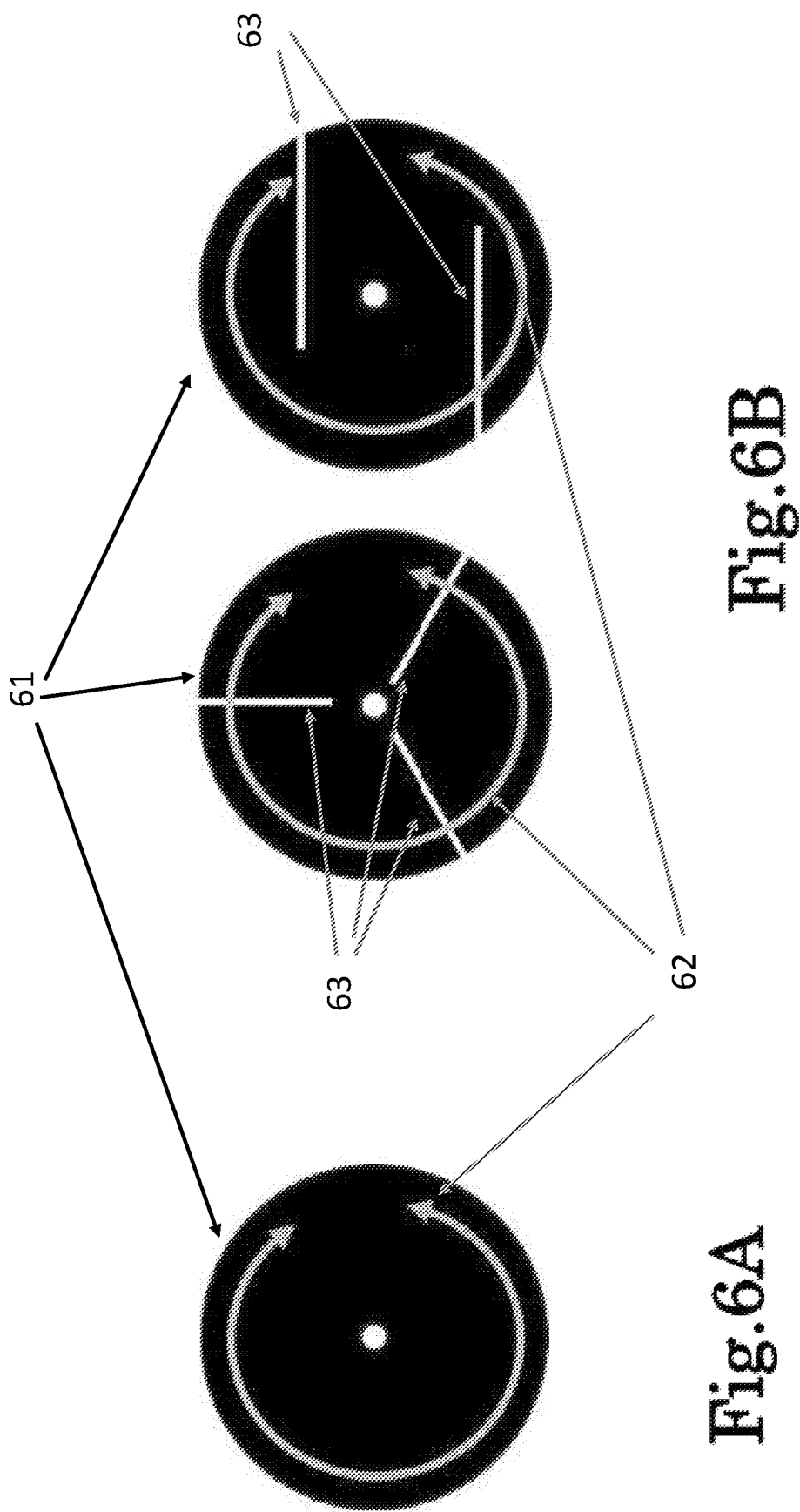

MAGNETIC DEVICE FOR TREATING LIVING TISSUES

CROSS REFERENCE TO RELATED APPLICATIONS

This application is the U.S. national phase of PCT Application No. PCT/IL2018/050831 filed on Jul. 26, 2018, which claims priority from Israeli Patent Application No. 253677, filed Jul. 26, 2017, entitled "MAGNETIC DEVICE FOR TREATING LIVING TISSUES", which is incorporated in its entirety herein by reference.

FIELD OF THE INVENTION

The present invention relates to treating biological tissues, more particularly to a magnetic device for directing energy to living tissues with high output and with improved focusing mechanism.

BACKGROUND OF THE INVENTION

The effects of magnetic fields on animals have been employed in various medical treatments (US 2010/0130945). An important treatment target is epithelial tissue. Epithelial tissue surfaces constitute a mechanical barrier against external harmful factors, and although they belong to key components of the body's defense, many details of their function remain unknown. For example, corneal epithelium blocks the penetration of harmful substances, but also polarized substances such as water and ions, into the anterior chamber, and an impairment in the corneal barrier leads to pain, chronic symptoms, injury, or even vision loss. US 2002/0035358 describes a method for treating corneal ulcers with electromagnetic pulses. WO 2014/181327 describes a magnetic device for treating an eye. U.S. Pat. No. 8,246,529 describes a method and a magnetic device for treating neurological disorders. The device includes a magnetic core made of a ferromagnetic powder.

The existing systems have several drawbacks. Some of the published systems aim at employing relatively weak magnetic fields; for example, US 2010/0130945 employs fields of nT to µT strength, and do not relate to the problems associated with employing stronger fields or overcoming such problems.

Also, the known systems do not sufficiently address the efficiency of the magnetic energy transfer to the treated tissue; the losses that may result, for example, from low conversion of the electrical energy; or from inefficiently directing the magnetic energy flow. Furthermore, heat losses constitute a double problem: low energy efficiency and overheating of the device parts. Such overheating may lower the device lifetime or require expensive and/or large heat dissipation means. Of course, all the mentioned problems are interconnected and will be more prominent for stronger magnetic fields.

It would be highly advantageous to have a system or method that could enable treating living tissues with magnetic fields in a broad range of the field intensities.

SUMMARY OF THE INVENTION

According to some embodiments, device for treating a living tissue with magnetic fields is provided, the device including one or more coil applicators; and a generator configured to drive a stimulation coil that is housed within the coil applicator that faces a tissue being treated, wherein the device is configured to provide a magnetic field in a range of at least 0.1 T to 3 T at a distance of 1 cm or less from the coil applicator(s) face.

In further embodiments, the coil applicator includes a stimulating coil with a core and windings; a ferromagnetic reflector plate adjacent to the stimulating coil, the ferromagnetic plate having a plane defining a rear side and a front side of the stimulating coil, the front side being oriented toward the tissue and the rear side being oriented facing away from the tissue; and a cooling mechanism configured to cool the stimulating coil.

In further embodiments, the core is a ferromagnetic core disposed within the stimulating coil and the ferromagnetic plate is adjacent to the stimulating coil and to the core. In further embodiments, the ferromagnetic reflector plate includes a groove for a lead/wire that electrically connects the coil with circuitry.

In further embodiments, an air flow shell with openings is provided, the shell enclosing the stimulating coil and configured to enable air to flow around the coil and the plate, and to prevent contact between the tissue and the coil.

In further embodiments, the cooling mechanism includes a heat sink and cooling fan.

In further embodiments, the generator is configured to generate magnetic pulses having an amplitude of up to about 3 T, length of 50 to 2000 µs, frequency up to 200 pulses/s, and a rate of change of at least 1000 T/s.

In further embodiments, the core and the plate are configured to form a ferromagnetic body that reflects the magnetic field created in the coil towards the treated tissue, thereby minimizing the energy losses and the cooling requirements. In further embodiments, the core and the plate are made of reactive sintered iron.

In further embodiments, the heat sink includes a flat, heat-conductive portion adjacent to the ferromagnetic plate, the heat-conductive portion including a groove configured to reduce eddy currents.

In further embodiments, the ferromagnetic plate and the flat heat-conductive portion are formed in a shape of two flat members connected in a heat-conductive interface.

In further embodiments, an apparatus is provided that is configured to fix the position of the tissue at a distance from the coil and a direction with respect to the coil. In further embodiments, the distance is 10 mm or less.

In further embodiments, the device has a shape in the form of eyeglasses.

In further embodiments, the apparatus includes a set of joints, axes and levers thereby providing the device with multiple degrees of freedom of movement.

In further embodiments, the device includes one or more spacers defining a distance between the coil and the treated tissue. In further embodiments, the spacer includes an insulating layer having a thickness of 10 mm or less. In further embodiments, the spacer includes an insulating layer having a thickness of 2 mm or less.

In further embodiments, the apparatus includes a resting place for a human chin and/or forehead.

In further embodiments, the device is configured to provide a magnetic field in a range of 0.1 T to 5 T at a distance of 1 cm or less from the coil applicator face.

According to some embodiments, a method is provided for treating a living tissue with magnetic fields in a wide range of strength, including providing a tissue stimulating magnetic field having an intensity of up to 5 T at a distance of 10 mm or less from the tissue.

In further embodiments, the stimulating magnetic field is applied to a tissue of a human organ, and the organ is afflicted with a condition selected from the group consisting of: an eye condition, including dry eye and mechanical ablation; a neurological disorder; a condition associated with pathological proliferation; and a pathology associated with epithelial tissues.

In further embodiments, the magnetic field intensity includes pulses having an amplitude of up to 5 T, a length of 50 to 2000 μs, a frequency up to 200 pulses/s, and a rate of change of at least 200 T/s. In further embodiments, the frequency is up to 1,000 T/s.

Embodiments of one aspect of the present invention provide a device for treating a living tissue with magnetic fields in a wide energy range, for example between 0.1 T and 3 T, including (i) a stimulating coil for creating a magnetic field of from 0.1 T to 3 T at a distance of about 1 cm from the coil; (ii) a low conductivity ferromagnetic core, situated within the coil; (iii) a low conductivity ferromagnetic plate, adjacent to the coil and in contact with the core, the plane of the plate defining the front side and the rear side of the stimulating coil, which radiates the energy of the magnetic field and the electric field to the treated tissue, in use the front side being oriented toward the treated tissue and the rear side facing away from the eye The plate preferably includes a hole or groove for leads connecting the coil on the front side with the energy source and/or the circuitry on the rear side; (iv) cooling mechanism including a fan and a heat sink; and (v) an air flow shell with openings, enclosing the stimulating coil and the cooling means, enabling the air to flow around or through the coil, the plate, and the heat sink, and configured to prevent contact between the tissue and the coil. The plate may be circular. The plate may form one solid block with the core.

In some embodiments, the device includes one or more coils, and a generator connected with the coil(s) configured to generate magnetic pulses having an amplitude of up to 5 T, a length of 50 to 2000 μs, a frequency of up to 200 pulses/s, and a rate of change of at least 200 T/s. These magnetic pulses induce electric field pulses in the tissue having an amplitude of up to 300 Volts per meter.

In some embodiments, the core and the plate form a ferromagnetic body focusing and reflecting the magnetic field created in the coil towards the treated tissue, thereby minimizing the energy losses and the cooling requirements. The core and the plate are made of a material exhibiting low power losses at kHz frequencies. In some embodiments, the materials include reactive sintered iron.

In some embodiments, the device includes an efficient cooling means including at least one fan and a heat sink. In some embodiments, the heat sink includes a flat portion adjacent to the ferromagnetic plate and is configured to prevent circular electrical currents (eddy currents) in the plane of the plate, such as at least one groove shaped to prevent the circular electrical currents. The core and the reflector plate constitute a focusing mechanism of the device, enabling a high output delivery of the magnetic field energy in a desired direction into a biological tissue.

In some embodiments, the device's heat sink includes a flat heat-conductive portion adjacent to the ferromagnetic plate. In some embodiments, the ferromagnetic plate and the flat portion have a shape of two flat cylinders being connected in a heat-conductive interface, for example a circular-shaped interface.

In some embodiments, the magnetic device includes an apparatus for fixing the mutual position, including distance and orientation, of the treated tissue and the coil. Predetermined distance and direction of the tissue toward the coil, as well as the magnetic signal strength and shape, is determined by the user, in accordance with the desired treatment. The predetermined distance is preferably 20 mm or less, for example 10 mm or less. In some embodiments, the apparatus includes a set of joints, axes, and levers that provide to the device several degrees of freedom of movement and enable one to direct the magnetic field in a broad range of intensities from desired distances and angles relative to the treated tissue.

In some embodiments, the device is configured as a hand-held instrument for easy handling by the user. In some embodiments, the device includes spacers defining the distance from the treated tissue to the coil radiating the energy of the magnetic field. The spacers may have a thickness of 10 mm or less, such as 2 mm or less. The spacers may also define the distance the device and the treated human subject; the distance may, in some applications, be 5 mm or less, in some applications 4 mm or less, in some applications 3 mm or less, in some applications 2 mm or less, and in some applications 1 mm or less.

In some embodiments, the treated tissue is a part of a human organ. In one embodiment, the tissue is a part of human eye. In one embodiment of the invention, the device includes an apparatus for fixing the position of the eye to be treated at predetermined distance from the coil, the apparatus including a resting place for a human chin and/or forehead. The device may have a shape of goggles or eyeglasses, or other suitable wearable devices.

In some embodiments, the apparatus has a fixed position or with a coarse adjustment mechanism, configured to allow the subject to lean there-against and achieve as accurate eye orbit position relative to the coil via an ergonomic interface.

Embodiments of another aspect of the present invention are directed to a method of treating a living tissue with magnetic fields in a wide range of strength, for example between 0.01 T and 5 T, such as 0.1 T to 3 T. The method includes creating a magnetic field of a desired intensity, in pulses having an amplitude of up to 5 T, a length of 50 to 2000 μs, a frequency up to 200 pulses/s, and a rate of change of at least 200 T/s, preferably at least 1000 T/s. Further, in some embodiments, the method may be executed by one or more of the following steps and related components i) positioning a nonconductive ferromagnetic core situated within the coil ii) operating a ferromagnetic plate (acting as a reflector), adjacent to the rear side of the stimulating coil, which coil is oriented toward the treated tissue with its front side; iii) operating cooling means including a fan and a heat sink; and iv) operating an air flow shell with openings, enclosing the stimulating coil, enabling the air to flow around or through the coil and the sink and cool them, and preventing the contact between the tissue and the coil. The sink preferably includes a heat-conductive flat part adjacent to the ferromagnetic plate, the part provided with at least one groove shaped to prevent circular electrical currents (eddy currents) within the flat part, for example one or more radial grooves, wherein both the plate and the flat part are preferably shaped as flat cylinders.

In some embodiments, the device preferably treats tissues which belongs to human organs, particularly organs afflicted with a condition selected from the group consisting of eye diseases including dry eye, neurological disorders, conditions associated with pathological proliferation, and pathologies associated with epithelial tissues.

In still further embodiments, the invention provides the use of the described device in treating a disease in a human subject in need of such treatment selected from the group consisting of eye diseases, neurological disorders, conditions associated with pathological proliferation, and pathologies associated with epithelial tissues.

In some embodiments, the invention provides the use of the magnetic device in treating epithelium-associated diseases. In a preferred embodiment, the device is used in treating an eye, for example in conditions including dry eye.

BRIEF DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein:

FIGS. 3A and 3B show a circular ferromagnetic plate in one block with a core for a device of the invention, according to some embodiments (FIG. 3A), and a circular ferromagnetic plate with a hole/pass for the coil lead in the device of the invention, according to some embodiments, and/or for attaching the heat sink (FIG. 3B);

FIG. 5B shows a cross-section of the stimulating coil and heat sink, which includes coil windings, the ferromagnetic core and reflector plate, and the heat sink, wherein the interface between the coil and the heat sink reaches closer to the windings, according to some embodiments;

FIG. 6A shows an example of a flat circular part of the heat sink, which is attached to the ferromagnetic plate in contact with the coil, and the direction of eddy current, according to some embodiments;

FIG. 6B shows a flat circular part of the heat sink, where grooving is used to diminish the eddy currents, according to some embodiments;

DETAILED DESCRIPTION OF EMBODIMENTS OF THE INVENTION

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In other instances, well-known methods, procedures, and components have not been described in detail so as not to obscure the present invention.

In some applications using the present invention, an afflicted epithelial tissue is treated with relatively strong and rapidly changing magnetic pulses, inducing electrical field in the tissue.

In some embodiments, a device is configured to magnetically treat animal or human tissues, and which creates a strong magnetic field and efficiently transfers its magnetic field and electric field energy to the treated tissue.

In some embodiments, the device is configured to magnetically treat animal or human tissues, and which efficiently directs the active magnetic and electric field pulses into the treated tissue.

In some embodiments, the device is configured so as to exhibit relatively low overheating.

In some embodiments, the device is configured to treat living tissues with magnetic and electric fields in a broad range of the field intensities and treating regimens, and in some embodiments the device is configured for safe and easy handling by experienced practitioners.

Figure 7:
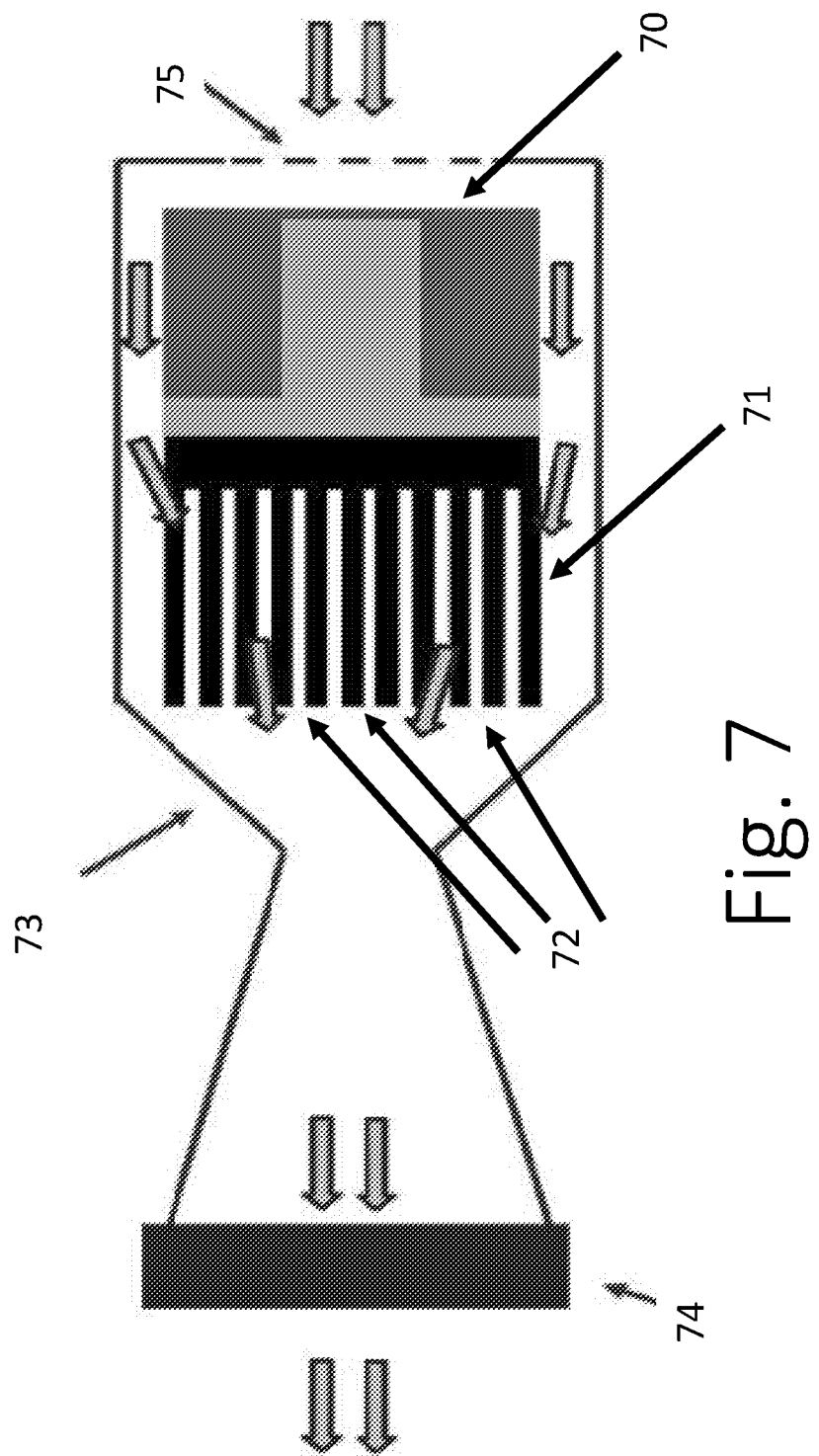
FIG. 7 shows an air cooling mechanism of an embodiment of the invention, where air openings are at the coil face and a fan is located behind it, with a funnel that forces the air to go through fins of the heat sink.
Figure 8:
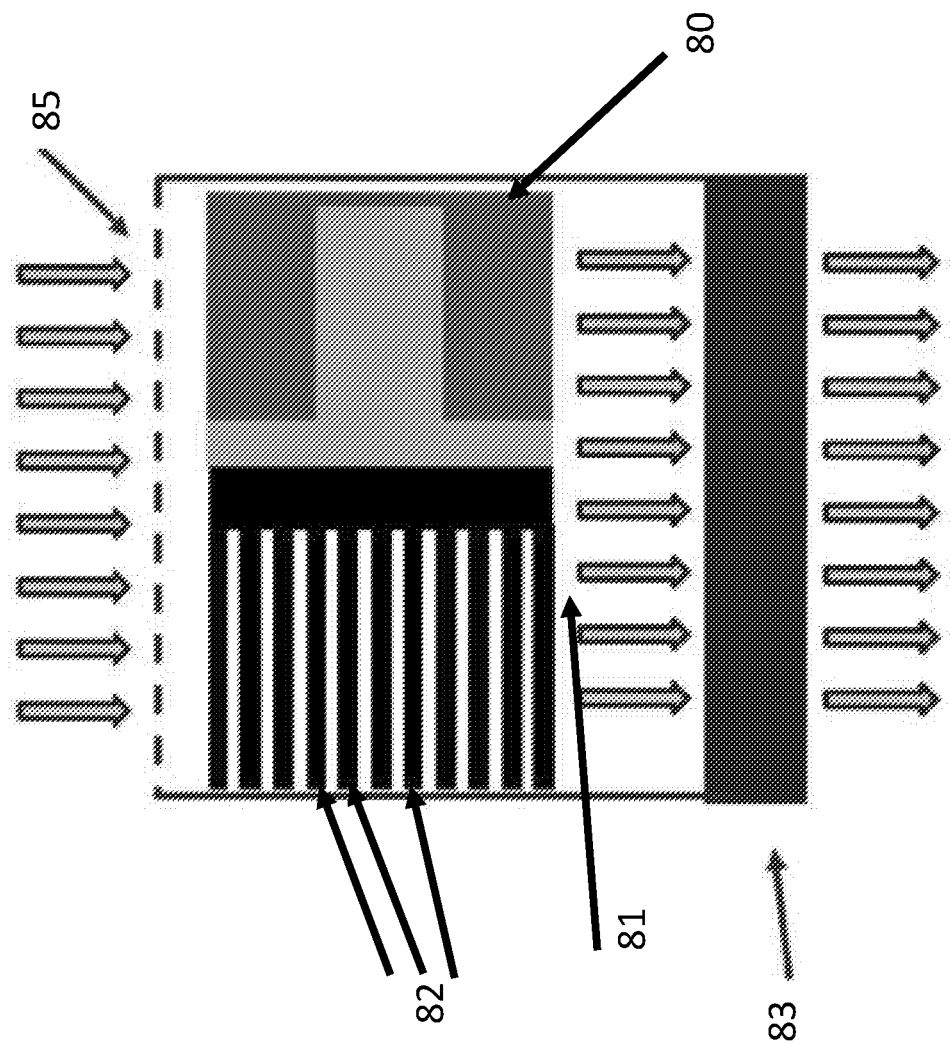
FIG. 8 shows an exemplary air cooling mechanism where the air openings and fan are located at the coil's perimeter, according to some embodiments.
Figure 9:
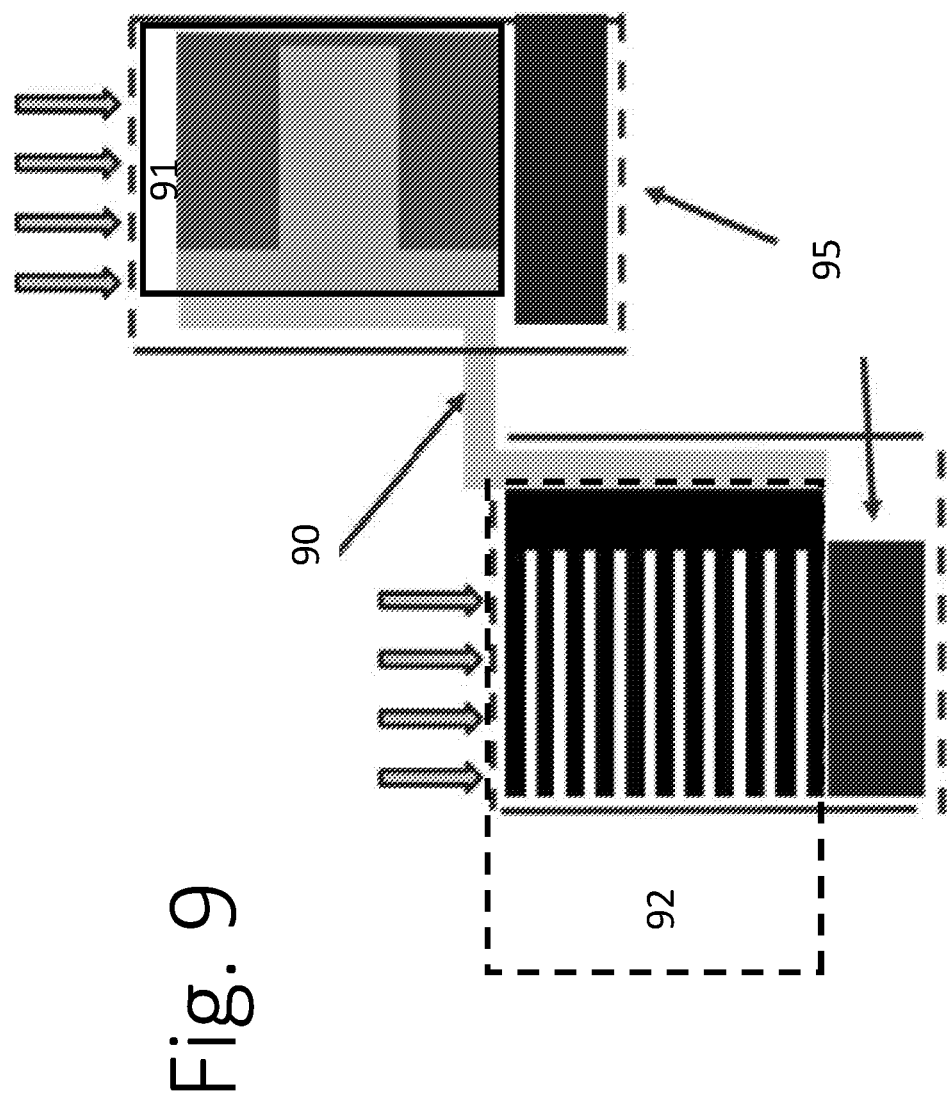
FIG. 9 shows an exemplary air cooling mechanism, according to some embodiments, including a heat pipe to transfer the heat away from the coil to a heat sink, which is located away from the tissue.

As described below, and with reference to respective figures below, a magnetic device 11 is provided with a coil having a core 32 producing a strong magnetic field, provided with an adjacent ferromagnetic base or reflector plate 33 and with a configuration to inhibit eddy currents and a suitable cooling mechanism as shown in FIGS. 7-9, directs the magnetic pulses to a treated tissue with surprising precision and energy efficiency. A device having the coil 14 can be advantageously employed for treating an ocular surface. A non-invasive magnetic stimulation device for the treatment of epithelium by repetitive magnetic stimulation according to the invention, for example for treating the corneal epithelium in the case of dry eye syndrome, includes a magnetic stimulator 16 driving one or more stimulating coils 14. The magnetic stimulator 16 may employ two or more coils intermittently, such as via two output connectors and appropriate control logic.

Figure 1B:
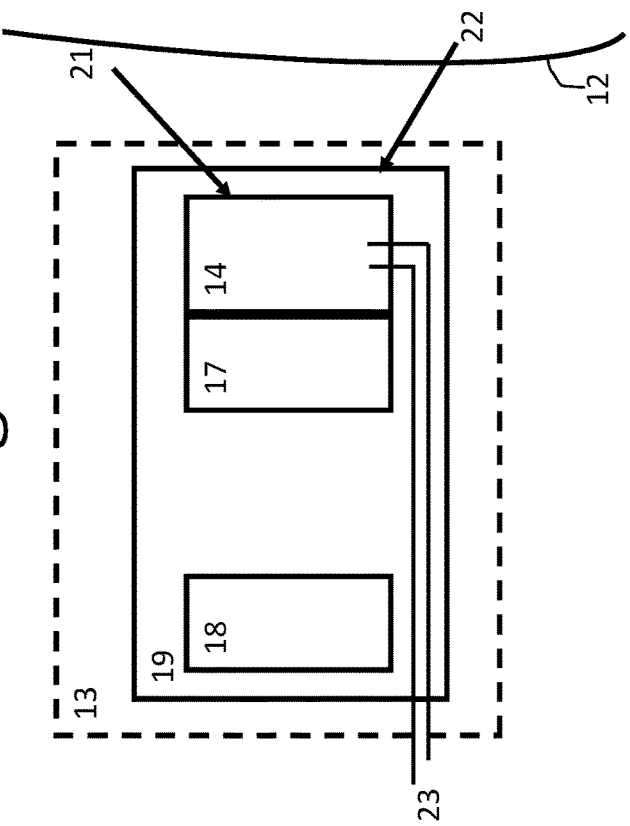
FIGS. 1A and 1B are schematic depictions of the structure of a magnetic device, in accordance with embodiments of the present invention, wherein a generator is driving a stimulation coil that is housed within a coil applicator that faces a tissue being treated.
Figure 1A:
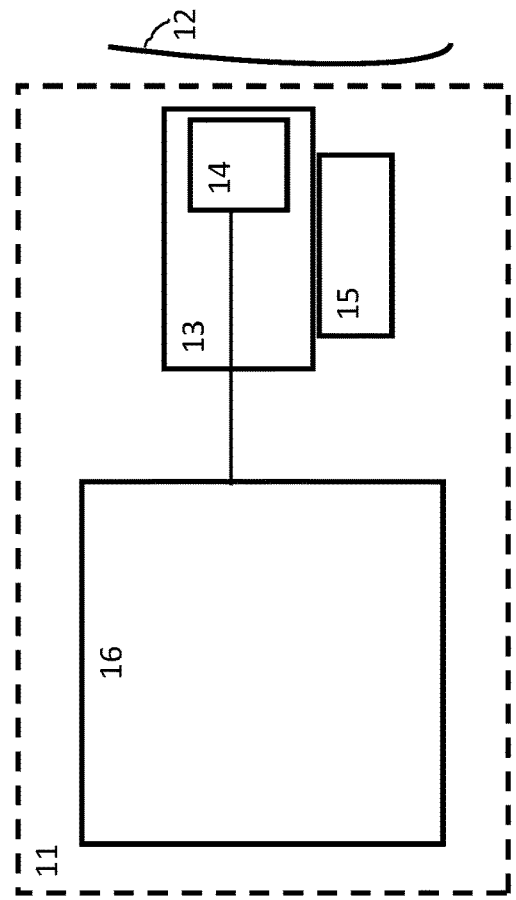

FIGS. 1A and 1B schematically show the structure of a magnetic device 11 according to some embodiments of the invention, wherein the front side of a stimulation coil 21 faces a tissue to be treated 12, with the coil 14 being disposed inside the shell 19, the entire coil applicator 13 is positioned relative to the tissue by apparatus 15, for example, object or mechanism for placing the applicators in front of the tissue to be treated. As can been with further reference to FIGS. 1A and 1B, the device 11 may include one or more coil applicators 13, each of which may include: a stimulating coil 14 and its driving wires 23, a cooling mechanism including a fan 18, a heat sink 17, and an air flow shell 19 with ventilation openings enclosing and insulating the above components from the user's contact. The insulation allows the user to bring the front side of the stimulating coil 21 to close proximity, such as less than 1 cm, to the treated tissue 12, such as a tissue that is a part of an organ requiring the treatment.

In the case of treating an ocular surface, for example for the treatment of dry eye disease, it is beneficial to stimulate afferent and efferent nerves passing through the foramina around the eye (supraorbital, infraorbital, lacrimal, efferent branches of the facial nerve, innervation of the Orbicularis and Riolan's muscle, etc.). In order to stimulate these nerves, a direct electrical stimulation by electrodes is suboptimal since it will require a large number of electrodes at various locations around the eye. Instead, a magnetically induced electric field can stimulate these nerves simultaneously without the need for any contact. Such electric field should have a peak intensity of for example 100 Volts/meter, at the target nerves, in order to be effective. The intensity is highly dependent on factors such as nerve morphology and alignment between electric field and nerve directions.

Figure 10:
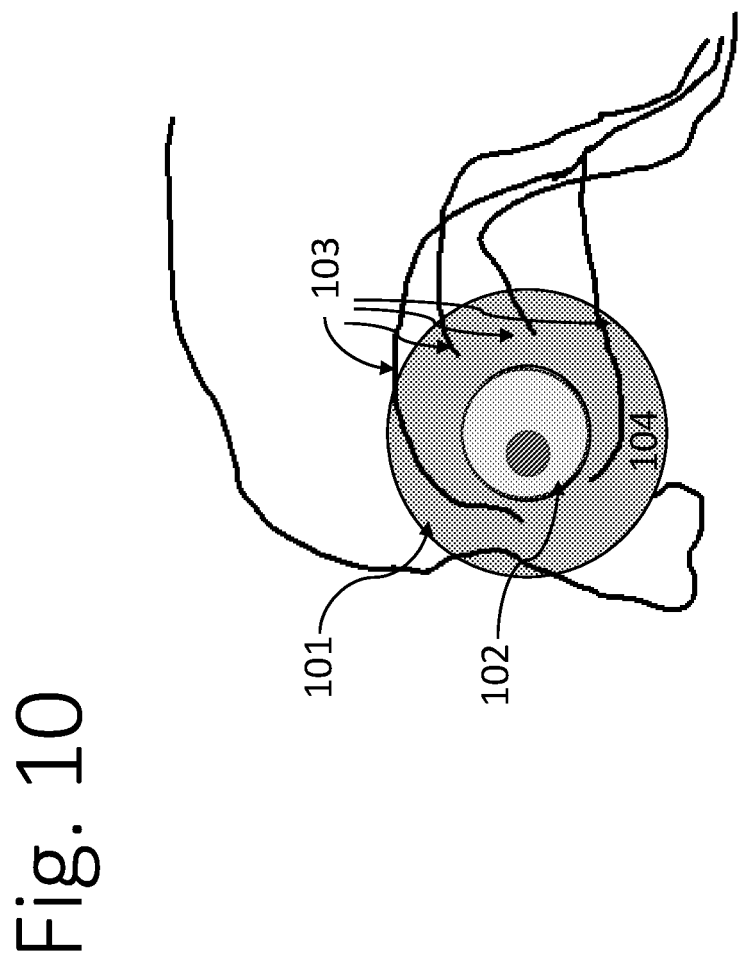
FIG. 10 shows an electric field ring around the eye ball or orbit affecting a plurality of nerves around and in the orbit, according to some embodiments.

In some embodiments, an electric field or activation ring 104 with a diameter of approximately 40 mm is optimal for targeting these nerves in an efficient manner in typical adults, as can be seen in FIG. 10, which shows the electric field ring 101 around the eye ball or orbit 102 affecting a plurality of nerves around and in the orbit. The diameter and width of the ring 101 can be changed to fit different patient sizes, to target different nerve groups or sub-groups and to reduce possible side effects such as tingling sensations.

In some embodiments, different sizes of "activating field(s)" may be provided, by using various coil sizes and reflector sizes. For example, coil size may or may not be optimized to include activation of the nerves inside the nose.

In other example, size may allow activating fewer or more nerves right around the orbit of the eye to minimize side effects.

In some embodiments, the activation ring 104 is efficiently attainable by an adequately designed magnetic coil that induces a circular electric field in the tissue, which is maximal at approximately 40 mm diameter and has an electric field intensity of sufficient amplitude in a diameter of, for example, 20-60 mm or 15-55 mm or 30-50 mm.

Figure 11:
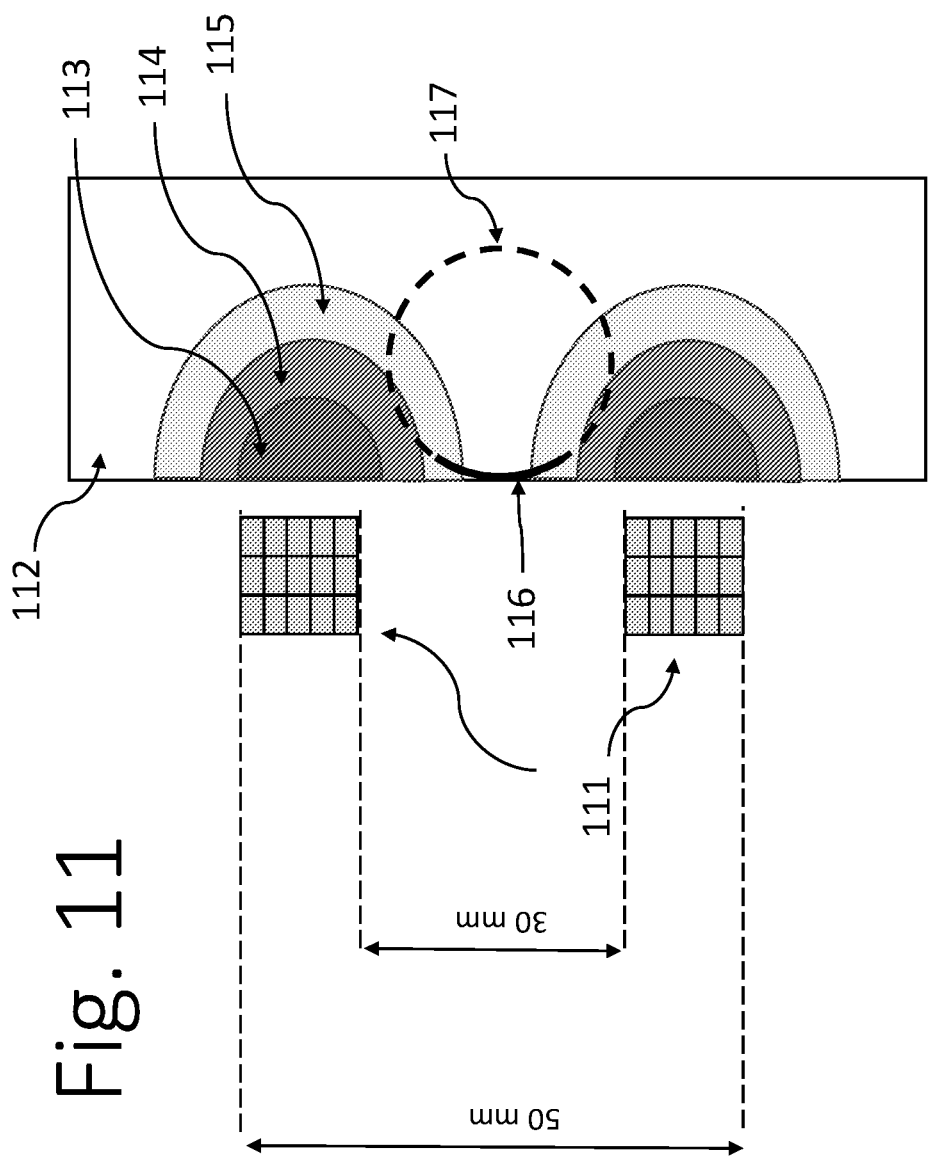
FIG. 11 shows a cross section of exemplary coil windings and treated tissue by induced electric field around the eye, also showing the intensity of the electric field decays with distance from the coil.

In order to obtain such activation pattern, according to some embodiments, a preferred choice is a circular coil that has an average winding diameter of about 40 mm, and a minimal and maximal winding diameter that are close to 40 mm, for example, a minimum winding diameter of 30 mm and a maximum winding diameter of 50 mm. Such a design also prevents exposure of ocular tissues such as cornea or retina to high intensity electrical field, as seen in FIG. 11, which shows a cross section of an example coil windings 111 and treated tissue 112 by an induced electric field 113-115 around the eye (cornea 116, retina 117). The intensity of the electric field decays with distance from the coil, e.g. the field has a high intensity. As can been in FIG. 11, the device may direct the electric field to various positions proximal to the coil, such that the closer to the coil, the stronger the field. The decay is continuous as the distance from the coil grows, but as can be seen in the shown example, position 113 has a strong field, position 114 has a weaker field, and position 115 has the weakest field, of these three example positions.

Figure 12:
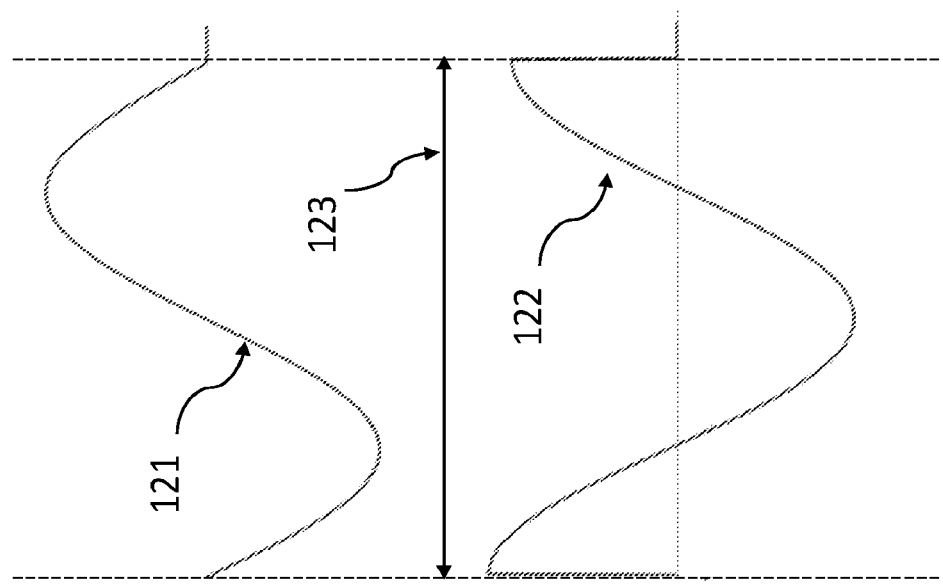
FIG. 12 shows an exemplary biphasic, sinusoidal, magnetic field pulse as a function of time, according to some embodiments, as well as an exemplary induced electric field of a cosine shape.

It is beneficial for the magnetic stimulation device to have a pulse duration of a few hundreds of microseconds, for example 300 microseconds. A typical magnetic stimulation device output magnetic field pulse is a biphasic sine shape, as seen in FIG. 12, which shows an exemplary biphasic, sinusoidal, magnetic field pulse 121 as a function of time. Also shown is an exemplary induced electric field of a cosine shape 122. The duration of the pulses in FIG. 12 is 0.0003 seconds or 300 microseconds 123.

Figure 19:
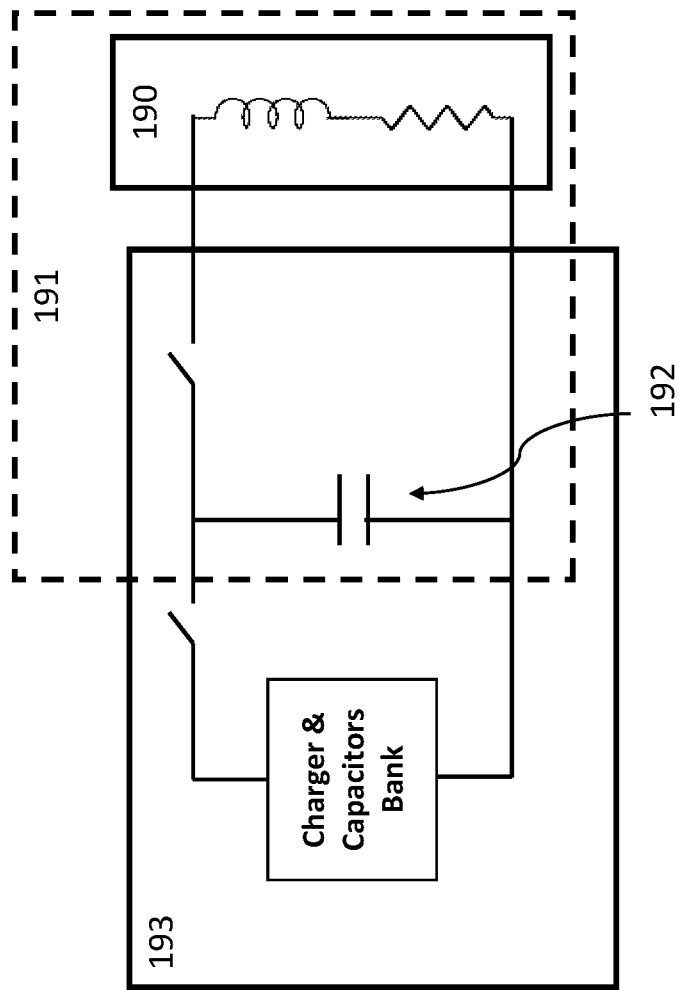
FIG. 19 shows a schematic electrical block diagram of the device, according to some embodiments, including a generator storage capacitor and stimulating coil.

As can be further seen, also with reference to FIG. 19, the device can be considered from an electrical circuit perspective, as an RLC circuit 191, which includes an energy storage capacitor 192 with capacitance C, a coil 190 with inductance L, and a total resistance R. Before the generation of the magnetic pulse, the energy storage capacitor 192 is charged with a voltage Vc0. The duration (or period) of the sine pulse is approximately $T=2\pi*\sqrt{(L*C)}$ when L is the inductance of the coil and C is the capacitance of the energy storage capacitor. The induced electric field is proportional to the time derivative of the magnetic field and therefore has a pulse with the cosine shape 122, with the same frequency or pulse duration. For example, if C=175 µF (micro Farad) and L=13 µH (micro Henri) the resulting pulse duration, or period, is approximately 300 microseconds 123. A similar pulse duration can be obtained using a different selection of C and L, providing that C*L is kept at approximately $2.3*10^{-9}$. Therefore, for example, if C=200 µF, L should be 11.5 µH. The frequency of the pulse in this case is approximately 3.3 Kilohertz. FIG. 12 is provided for conceptual illustration without specific intensity values.

In some cases, a generator with an energy storage capacitor of 175 µF may be operated with one or more of the following aforementioned design requirements: Average coil windings diameter of approximately 40 mm; Coil winding diameter range of 30-50 mm; Pulse duration of 300 microseconds; and Electric field peak value of 100 V/m e.g. 15 mm from the coil face.

Figure 13:
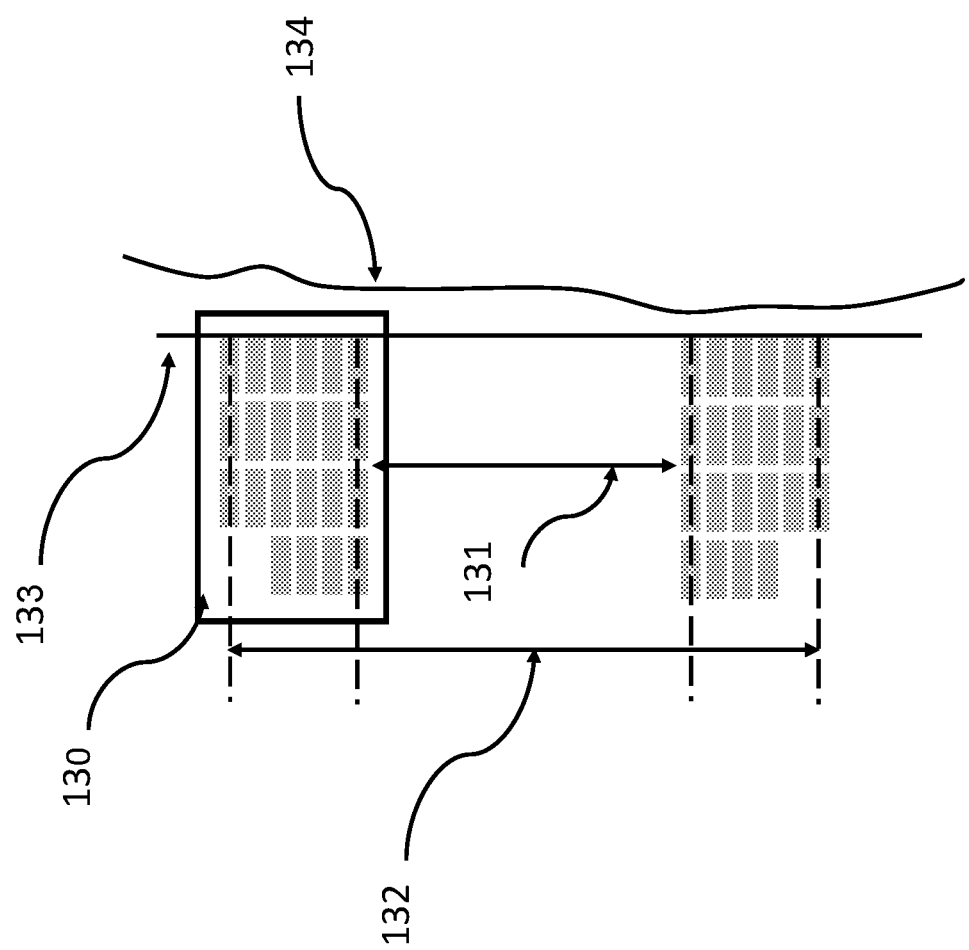
FIG. 13 shows a cross section of a coil with windings of copper conductor, according to some embodiments.

There are a number of design options for achieving these requirements. For example, the option shown in FIG. 13, which shows a cross section of a coil with 22 windings of copper conductor 130 with a minimum winding diameter 131 of approximately 13 mm and maximum winding diameter 132 of approximately 23 mm. 133 shows the coil's front side placed close to the tissue 134, according to some embodiments In order to obtain the above electric field requirement, 15 mm from the coil face, an initial capacitor voltage Vc0 is required to be approximately 1000 Volts, and the time averaged ohmic loss for a single pulse is approximately 110 KiloWatt.

Alternative ways to increase the pulse duration without increasing the number of coil windings could be to increase the capacitor inductance or add another coil in series to the stimulating coil. However, both of these alternatives are sub-optimal in the energetic efficiency.

In a preferred embodiment of the invention, the stimulating coil includes a ferromagnetic plate as a reflector that reflects the magnetic field towards the treated organ in order to minimize energy losses, minimize the cooling requirements, and make the coil more efficient. Such a reflector is schematically shown in FIG. 3A, which shows a circular ferromagnetic plate 30 in one block with a core for a device of the invention, according to one embodiment (FIG. 3A), and a circular ferromagnetic plate 30 with a hole/pass 34 for the coil lead in a device of the invention, according to an embodiment, and/or for attaching the heat sink (FIG. 3B). As can be seen, circular ferromagnetic plate 30 includes a core 32 on the front side, focusing the magnetic field so that the magnetic field passes more in the center of the coil (through the core). The core 32 also makes the stimulating coil production less sensitive to the exact position of the coil windings. The core 32 and reflector plate 33 increase the inductance of the coil and thereby increase the duration of the pulse for the same number of windings and windings geometry. For the same requirements as mentioned above, the coil with circular ferromagnetic plate 30 and a core 32 on the front side can be driven with an initial capacitor voltage Vc0 of approximately 700 volts, and resulting with a time averaged ohmic loss for a single pulse of approximately 50 Kilowatt. The reduction in ohmic loss per pulse is very important when stimulating the tissue at higher pulse rates than are typically used in brain stimulation, for example higher than 20 pulses/sec.

When employing conventional ferromagnetic materials in non-DC applications, the magnetic effects may be dramatically reduced by the formation of eddy currents, which for example reduce the time derivative of the magnetic field. The device according to the invention employs electromagnetic coils provided with ferromagnetic cores and ferromagnetic reflectors, which increases energy efficiency and reduces also the cooling requirements. The ferromagnetic material used for the ferromagnetic cores used in the invention is preferably reactive sintered iron; for example, mutually electrically insulated magnetic granules, for example such as Permedyn™, in the state of a solid body (non-powdered). Reactive sintered iron has low conductivity and a narrow hysteresis loop, therefore providing low eddy current and low hysteresis loss in frequencies up to 50 kHz.

An important property of the material for the coil and core according to the invention is its power loss at magnetic field changes in the kHz range. For example, if a pulse has a perfect single sine period shape and duration of 300 microseconds, its frequency will be 3.33 KHz. The pulse may differ from a perfect sine, and the rate of changes of the magnetic field may include a different range of frequencies. The materials suitable for the cores in a device according to the invention may exhibit power losses, for example, 150-750 W/kg at 0.5-1.0 T and 2-6 kHz, such as 200-400 W/kg. In some applications, the inventors observed that the total heat generated in the core and reflector was about 1% of the heat generated by the electrical current in the windings.

In some embodiments, the windings of the coil are typically electrically insulated by a thin coating layer (not shown). The windings are typically made of a wire of a fairly large cross-section (a few square mm) to maintain low electrical resistance and reduce the ohmic energy loss. A square cross section is often preferred to obtain optimal wires and current density. Alternatively, they can be in the form of a sheet (e.g. 0.5 mm thick), or of a round cross-section. The coil windings may include a combination of several types of windings in series, such as sheet and square cross-section wire. The windings may be molded in a thermally conductive epoxy encapsulation 57 or similar material in order to absorb the mechanical strain/shock to the coil windings by the electromagnetic pulses, and in order to improve the thermal conduction. An epoxy encapsulation can withstand an operating temperature of up to 130° C. In some examples, as can be seen with reference to FIG. 5, the core 51 and reflector plate 52 may have a thread 53 (FIG. 5A) for mounting of a heat sink 54 and a hole/pass/groove 45 in the reflector plate 52 to allow passing of the coil lead (wire) so that it does not protrude to the front side of the coil 43 (see FIG. 3 and FIG. 4). This is important because any protrusion of wires to that area would lead to a larger distance between the stimulating coil face (front side 43) and the treated organ 44.

Figure 4C:
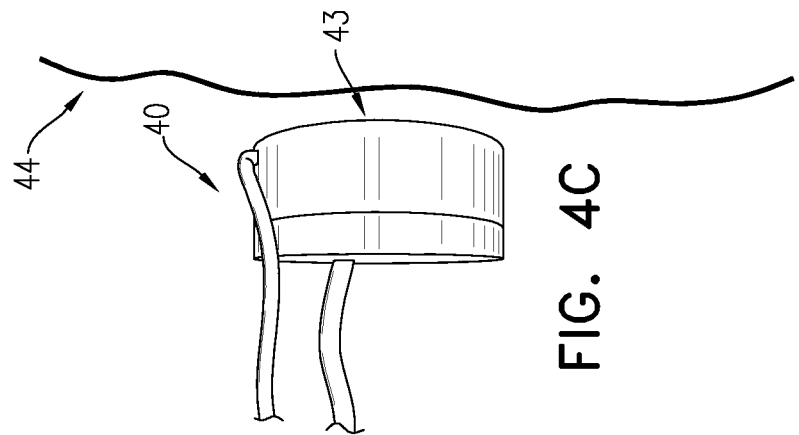
FIG. 4 shows a stimulating coil demonstrating a reflector plate (FIG. 4A or 4C) that precludes protruding of the lead/wire to a space between the stimulating coil and the treated organ (FIG. 4B), according to some embodiments.
Figure 4B:
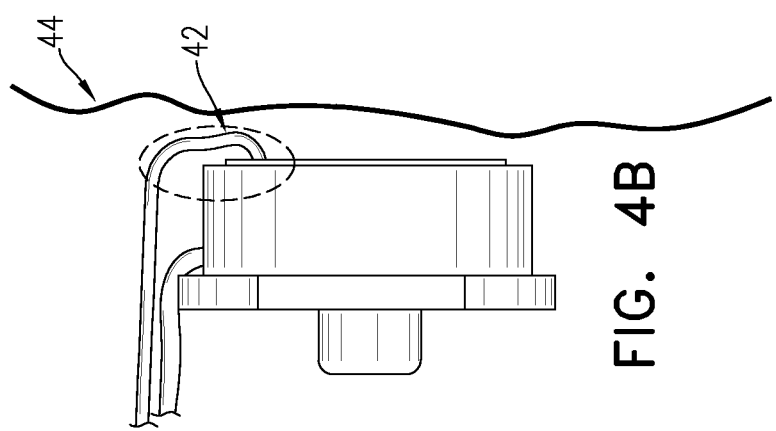
Figure 4A:
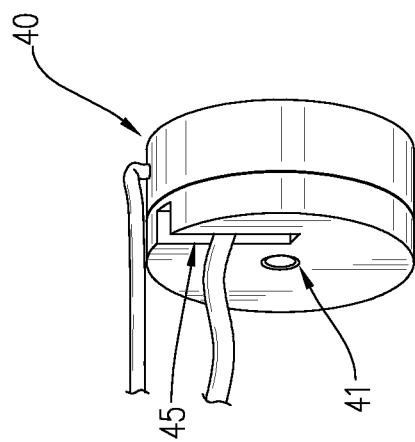

FIGS. 4A-4C show a stimulating coil 40 demonstrating how the pass in the plate 45 (FIG. 4A or 4C) precludes protruding of the lead (wire) to the space between the stimulating coil 40 and the treated organ or tissue (44), according to some embodiments. FIG. 4B shows such protrusion of a copper wire 42 out of the front side of the coil [40 between the area between the treated tissue 44 and the coil 40; this is avoided in embodiments shown in FIGS. 4A and 4C having a wire pass/hole 45 in the reflector plate.

Figure 5C:
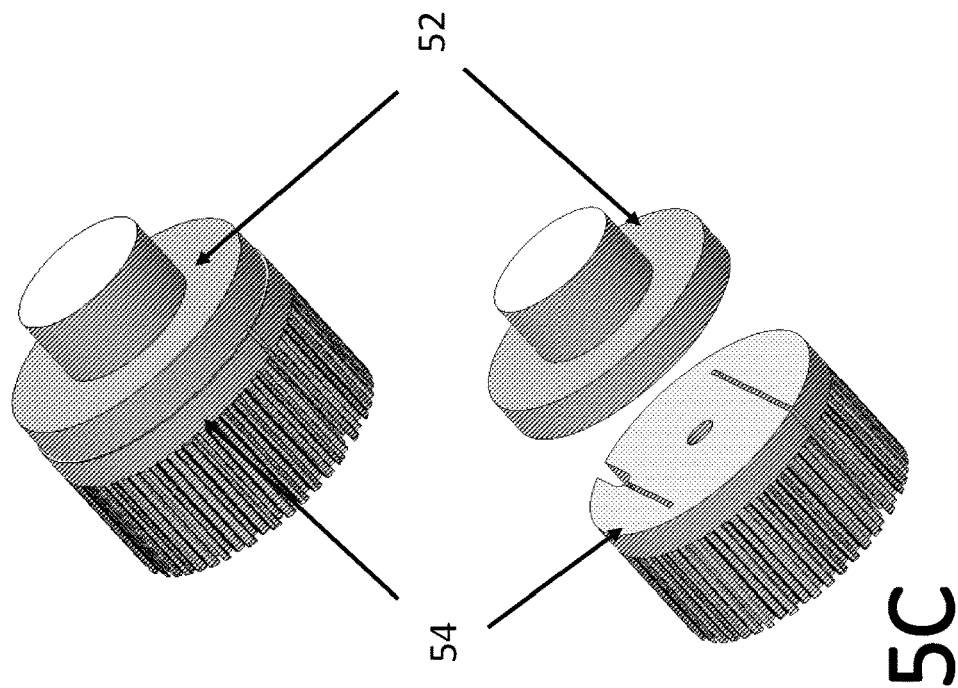
FIG. 5C shows a reflector, core and heat sink, according to some embodiments, attached together and separated.
Figure 5A:
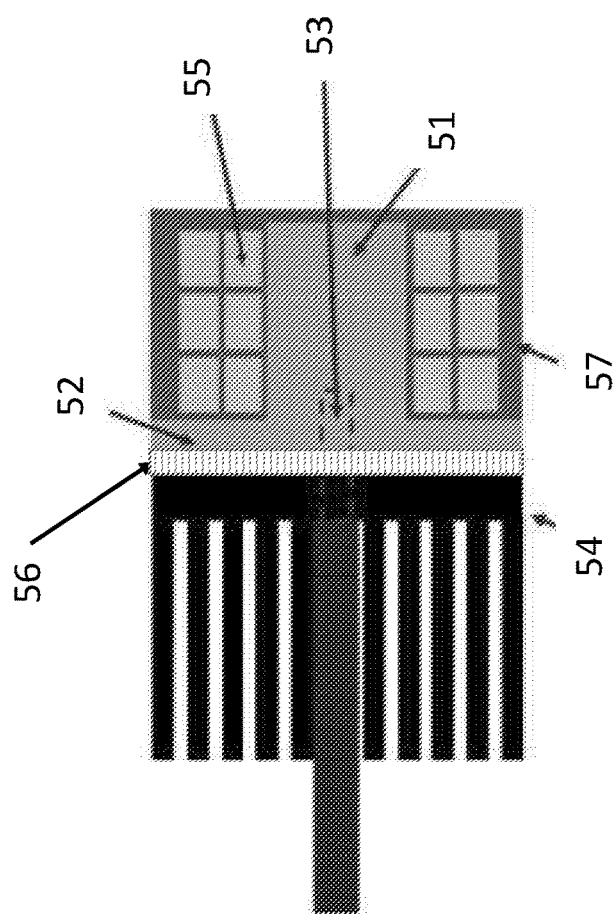
FIG. 5A shows a cross-section of the stimulating coil and heat sink, which includes coil windings, ferromagnetic core and reflector plate, and heat sink, wherein an example is shown of a heat sink, core and reflector, attachable by a screw, according to some embodiments.

In some embodiments, the thread 53 can facilitate the attachment of the heat sink 54 to the reflector plate 52, in some embodiments, as shown in FIG. 5A, which shows a cross-section of an assembly, which includes coil windings 55, ferromagnetic core 51, reflector plate 52, and heat sink 54, wherein the heat sink is attached to the plate or core by screw. In this case, the interface between the reflector plate 52 and the heat sink 54 may include a thermal paste 56 to provide for good heat transfer. The heat sink 54 may also be provided with a heat sink projection 59 and a male protrusion(s) 58 inserted into slots in the reflector plate 52 and/or around the reflector plate, as shown in FIG. 5B, which shows a cross-section of an assembly which includes coil windings, a ferromagnetic core and the reflector plate and a heat sink, wherein the interface between the coil and the heat sink reaches closer to the windings. A further example of the reflector plate and heat sink can be seen in FIG. 5C.

According to some embodiments, the heat sink has a hole/pass/groove to facilitate the passage of the conductive wires of the stimulating coil, in a similar fashion as the reflector plate. Since the heat-conductive heat sink is usually made of metals of high electrical conductivity such as aluminum or copper, the magnetic field will induce circular eddy currents in its base, as shown by the arrows 62 in FIG. 6A, which shows a flat circular part of the heat sink 61 which is to be attached to the ferromagnetic plate in contact with the coil, and the direction of eddy current 62, according to some embodiments. This would lead to generating heat within the heat sink. To prevent this, thin grooves 63 may be cut in the heat sink base according to some embodiments, reducing the undesired eddy current effect. Grooves of various shapes and directions may be employed, examples of which are shown in FIG. 6B, which shows a flat circular part of the heat sink 61, where grooves 63 diminish the eddy currents 62, according to some embodiments.

In some embodiments, it is preferred to remove the heat both through the heat sink and directly from the face of the epoxy or from the coil windings, particularly when non-uniform generation of heat in the windings occurs or when the reflector plate and the core materials do not exhibit optimal thermal conductivity. In some embodiments, an air cooling system is employed including air clearances 75 in the coil applicator face (as schematically shown in FIG. 7) to facilitate the flow of air on the coil epoxy encapsulation 70, wherein a tunnel in the shape of a funnel 73 forces the air flow within the inner fins of the heat sink 72, the air flow being mainly perpendicular to the face of the stimulating coil.

In some embodiments, the air cooling system (FIG. 8) includes an air flow mainly parallel to the face of the stimulating coil 80 and through the heat sink 81. The heat sink fins 82 may have a spike shape or preferably a plate shape to maximize their surface area and to reduce air flow turbulence. The fan 83 either pushes the air or preferably pulls the air, using cooling air clearances 85.

In some embodiments, the air cooling may also include the use of a heat pipe 90, for example, in order to transfer the heat away from the coil 91 to the heat sink 92, for example as schematically shown in FIG. 9. This arrangement may be used to minimize the size of the part of the coil applicator that is put in proximity to the target organ, or to incorporate a commercial cooling module (heat sink with fan), including cooling fans 95.

The coil applicator 13 may include one or more sensors (not shown) that measure the temperature within the coils flow shell 19 and convey the measurement to the magnetic stimulator 16 as a part of a safety mechanism to prevent overheating in the case of a failure in the cooling mechanism.

The device according to the invention enables management of intensive heat formation in treatments with strong fields of 1 T or more, when the coil currents may reach the values 1000 amperes or more, and when employing large frequencies (even thousands of Hz). Such conditions would otherwise overheat the device without efficient cooling; moreover, the energy input would be too high without the device's focusing mechanism (constituted by the core and reflector plate), which increases the energy efficiency by reducing the magnetic field outside the region of treatment.

In the case of treating ocular surface diseases, such as dry eye, in some embodiments, two devices can be so as to treat both eyes simultaneously. The device may include an apparatus (15) for fixing the position of the patient's target organ, such as a chin and forehead rest for fixing the position of the eye in the case of an ocular application. The device may include an apparatus that is used to control the position and the orientation of the coil applicator(s) relative to the treated organ of the patient. The apparatus allows for precise positioning of the stimulating coils within close proximity to the organ so the net distance between the face of the coil and the target organ is less than 1 cm, and in some cases a minimal insulating layer of as low as 1 mm will serve as a spacer. This apparatus can include a set of joints, axes and levers, which provide several degrees of freedom of position control.

Figure 2:
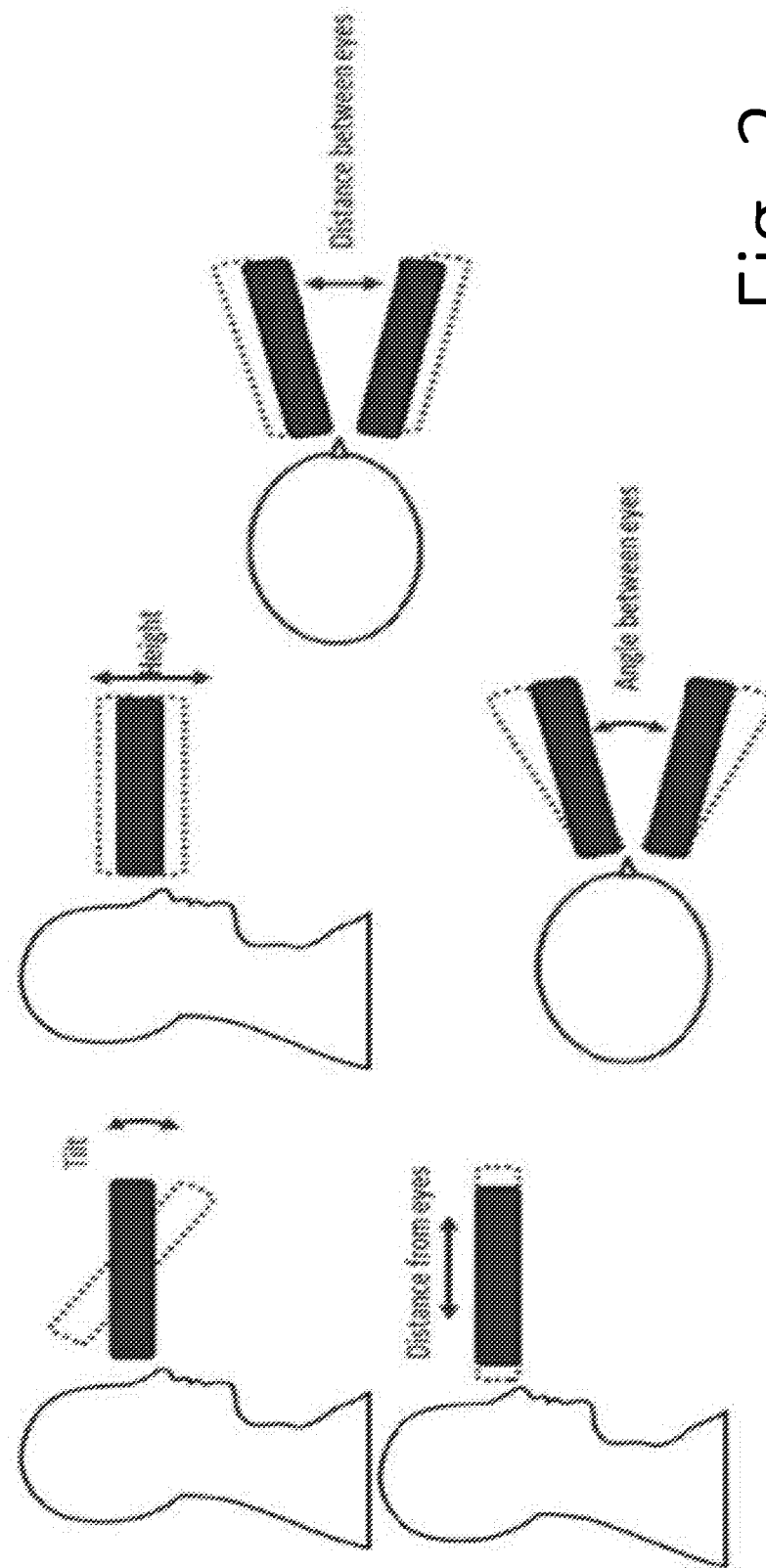
FIG. 2 shows the degrees of control over the position of the coils relative to the eyes for case of treating eyes tissues, according to some embodiments.

FIG. 2 shows the degrees of control over the position of the coil applicators relative to the eyes for case of treating eyes tissues, according to some embodiments, for the case of ocular treatment. The coil applicator can be handheld by a user/operator/patient in proximity or adjacently to the target organ, or spacers may be employed, such as a rubber ring. In case of an ophthalmic device, an eyecup may be included, for example such as used in binoculars. The coil applicator preferably has a size and shape enabling placement adjacent to the treated organ, for example within the eye orbit. The coil applicator may include a visual mark on its frontal face, corresponding to the center of stimulating coil, to facilitate accurate positioning in the center of the eye visual field and orbit. In one embodiment, the device includes a motorized table, such as often used for ophthalmic procedures (for example for slit lamp bio-microscopy). The motorized table can allow height adjustment of the position of the device to allow seating the patient comfortably, both for the patient and the examiner. After adjusting the height of the ophthalmic table and chin rest, the coil applicators are placed near the patient eyes to be treated. The placement of the coil applicators adjacently to the eyes is achieved by setting the height of the ophthalmic table according to the patient body size, setting the chin rest height for a comfortable sitting position, and adjusting the position and orientation of the coil applicators relative to the eyes.

Figure 16:
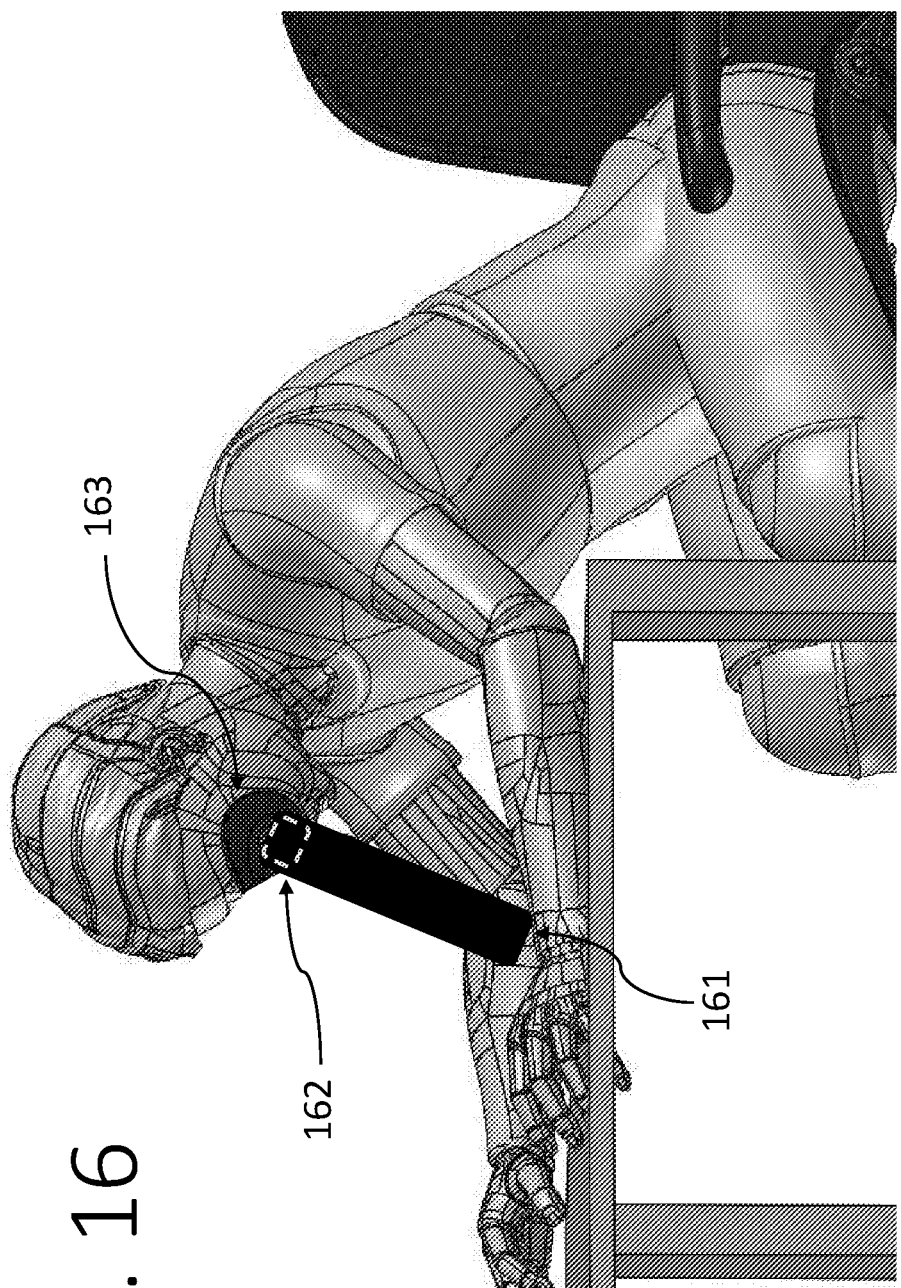
FIG. 16 shows a conceptual example of a table-top apparatus having a coil in proximity to a human patient's eye, when the patient is leaning toward the apparatus, against an ergonomic interface 163, according to some embodiments.

In accordance with some embodiments, the coil applicator is configured or adjusted in a broad or coarse way, thereby leaving the fine positioning for the human patient to perform. FIG. 16 illustrates a conceptual example of a table-top apparatus 161 having a stimulating coil 162 in proximity to the human patient's eye, when the human patient is leaning toward the apparatus, against some ergonomic interface 163, according to some embodiments. As can be seen, the coil applicator(s) may be positioned on a table top with an ergonomic interface 163 that guides the patient to correctly position the eye or orbit in the correct position relative to the stimulating coil 162. This can be done using a material that can absorb the patient's head weight and features such as foam rubber or silicone, shaped to fit typical facial features around the orbit such as the shape of the bones around the orbit, and the shape of the nasal bridge.

As can be seen in FIG. 16, the alignment of the electromagnetic field around the eye's orbit and the innervation just outside the orbit is an anatomical optimization that enables consistent focusing on the same spot for each patient (+/−0.5 cm tolerance max).

Figure 17:
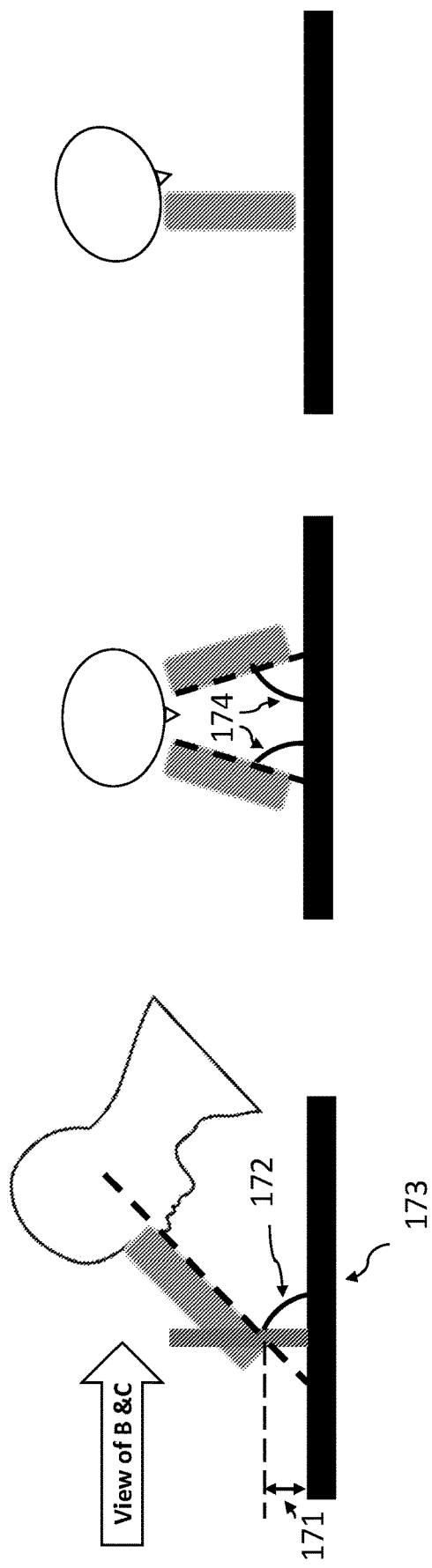
FIGS. 17A-17C show several configurations of a table top apparatus, according to some embodiments, FIG. 17A showing a side projection of the apparatus, FIG. 17B showing two coil applicators for two eyes, and FIG. 17C showing a single coil applicator and human subject turning his/her head to place the eye/orbit in front of it.

FIGS. 17A-17C show several configurations of a table top apparatus, according to some embodiments. FIG. 17A shows a side projection of the apparatus with height 171 and tilt 172 relative to the table top 173 either fixed or controllable. FIG. 17B shows two coil applicators for two eyes, where the angles 174 may be either fixed or controllable. FIG. 17C shows a single coil applicator and human subject turning his/her head to place the eye/orbit in front of the device. The apparatus may include control over height and tilt (FIG. 17A) and/or turn (FIG. 17B). The apparatus may have some suspension mechanism to which the coil is harnessed, so that when contacted with the patient's face the coil is forced to the accurate position and orientation relative to the patient's orbit.

In another configuration, the ergonomic interface may be made of a disposable material and replaced with a new one for every treatment. In another configuration, the ergonomic disposable interface may be fitted for each patient in a personalized manner, such as creating an imprint of the facial structure of the patient around the eye so it achieves accurate positioning relative to the patient facial features such as the bones around the orbit, and nasal bridge. Such ergonomic disposable interface may be made in a similar manner to a radiotherapy mask, producing a form that may be attachable to a coil applicator intended to provide and/or enhance alignment and repeated re-alignment for the intent of electromagnetic stimulation of peripheral nerve tissue in the vicinity of the eye.

Figure 18:
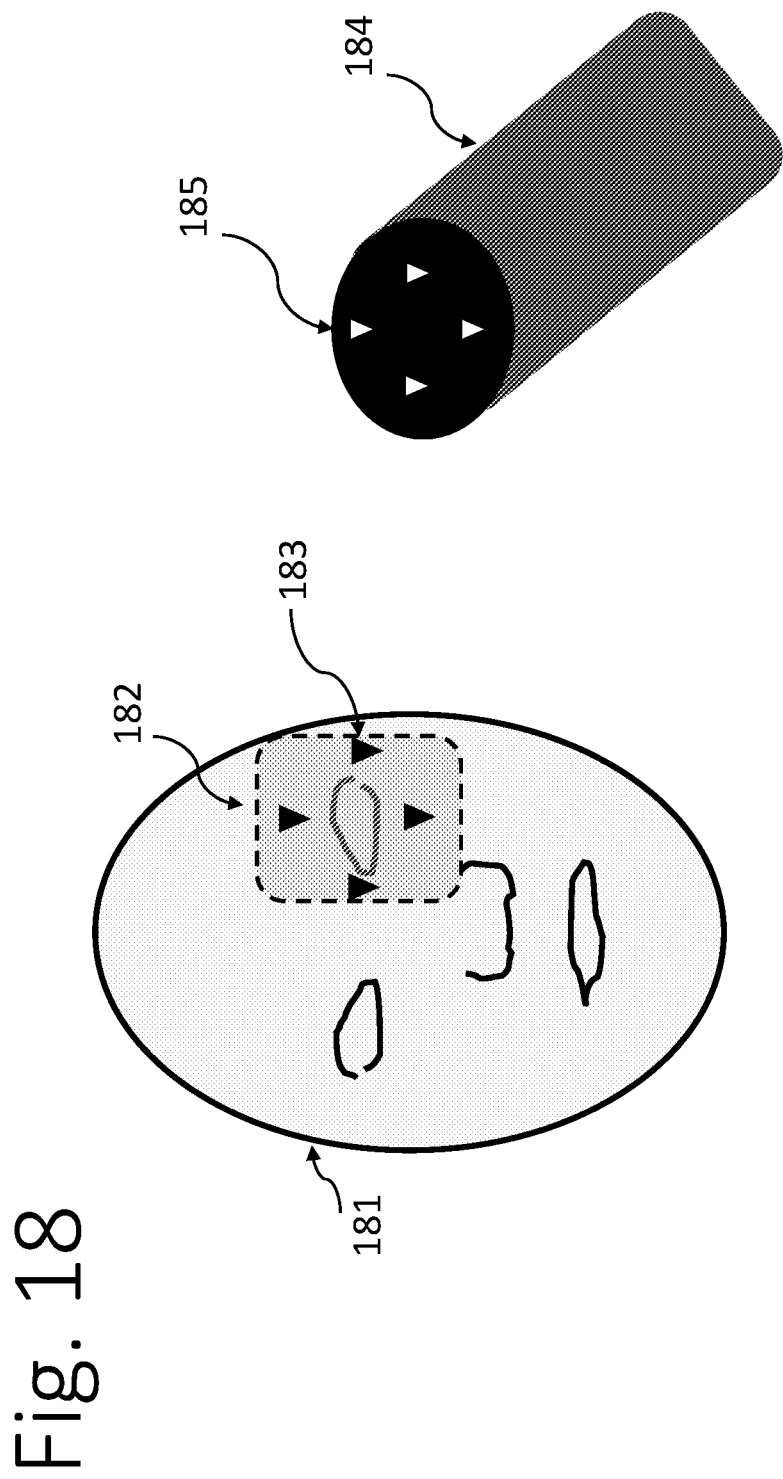
FIG. 18 shows a human patient's face, with an ergonomic patient specific interface.

After the interface has been shaped according to the patient's facial features, additional positioning may be required of additional elements such as male snap connectors, relative to the facial features, and these connectors will serve as an interface to female snap connectors on the coil applicator, as shown in FIG. 18. As can be seen, a human patient's face 181 may be provided with ergonomic patient specific interface 182, which has four connectors, such as male snap connectors 183, according to some embodiments. Also shown is a coil applicator 184 with four matching connectors such as female snap connectors 185.

In some embodiments, the facial attachment may form an imprint from the face; in one example, similar to a plastic "mesh" used for gamma knife radiation fixation etc. In a further example, an impression may be made with "smooth on facial silicone" or in other suitable ways.

In still further embodiments, the coil applicator may be part of a table top apparatus or positioned using glasses or other suitable wearable member, to help place the coil applicators of the device opposite or proximal to a specific location(s). In some cases, the wearable device may have customization to keep in proper place, e.g. flexible material to form an optimized fit.

In some embodiments, the method includes forming an imprint of a facial structure such as the area surrounding the eye or a mammal, both eyes of a mammal, the eyes and the nose of a mammal or the entire forehead and the eyes of a mammal, or the entire forehead and face of a mammal to generate a form that may be attachable to n coil applicator intended to provide and/or enhance alignment and repeated re-alignment for the intent of electromagnetic stimulation of peripheral nerve tissue in the vicinity of the eye.

Embodiments of the present invention will be further described and illustrated by the following examples.

In a first pilot study for testing the safety of repetitive magnetic stimulation for the treatment of dry eye, the study was registered with ClinicalTrials.gov Identifier No. NCT03012698. The study was an Interventional study type and the treatment employed repeated magnetic stimulation (RMS) treatment to the eye. The study tested the safety of RMS for treating dry eye. Patients were asked to undergo a one-time treatment with an EpiTech Corneal Magnetic Stimulation Device, a device according to some embodiments of the invention, on one eye. Changes were monitored for over a study period of 3 months. The study included males and females, 18-80 years old, with moderate to severe dry eye syndrome; the estimated enrollment was 30 patients. The data were processed in accordance with the requirements of the International Committee of Medical Journal Editors and the International Clinical Trials Registry Platform (ICTRP) of the WHO. Of the first five (5) patients, three (3) had Sjogren syndrome, one (1) had meibomian gland dysfunction and one (1) had aqueous deficiency not related to Sjogren syndrome.

Figure 14:
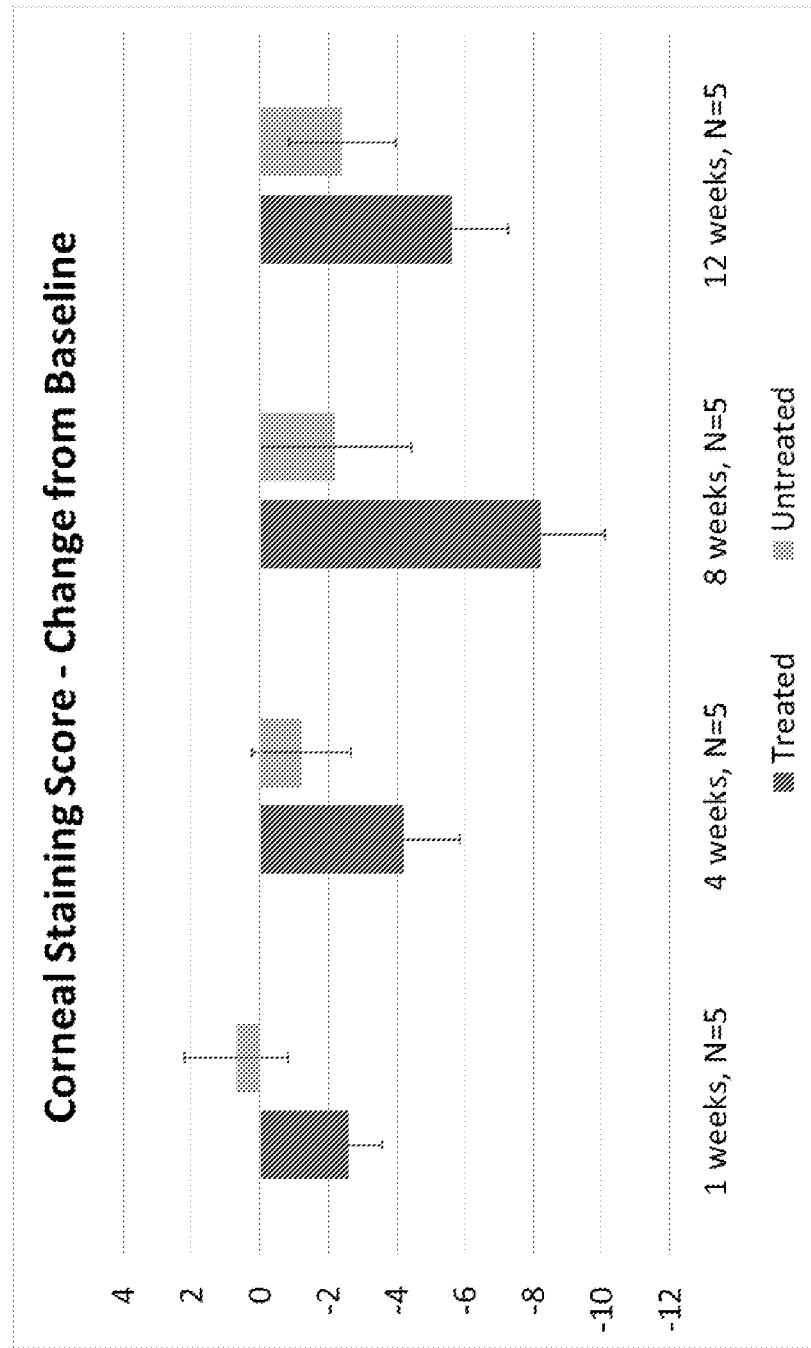
FIG. 14 shows clinical results of a corneal staining score change from baseline for a treated and untreated eye, according to some embodiments.

All patients tested completed a three month follow up. The reduction in corneal staining in the treated eye was significantly larger than in the untreated eye within one week after treatment, and appeared most prominent at eight weeks, as seen in FIG. 14. The untreated eye also showed some non-significant reduction in staining, suggesting there might be some treatment effect on the contralateral eye. Average change and standard error are shown for five patients at a follow-up at 1, 4, 8 and 12 weeks following treatment to one eye, and further showing that the corneal staining was graded according to the NEI/industry scoring on a scale of 0-15.

Figure 15:
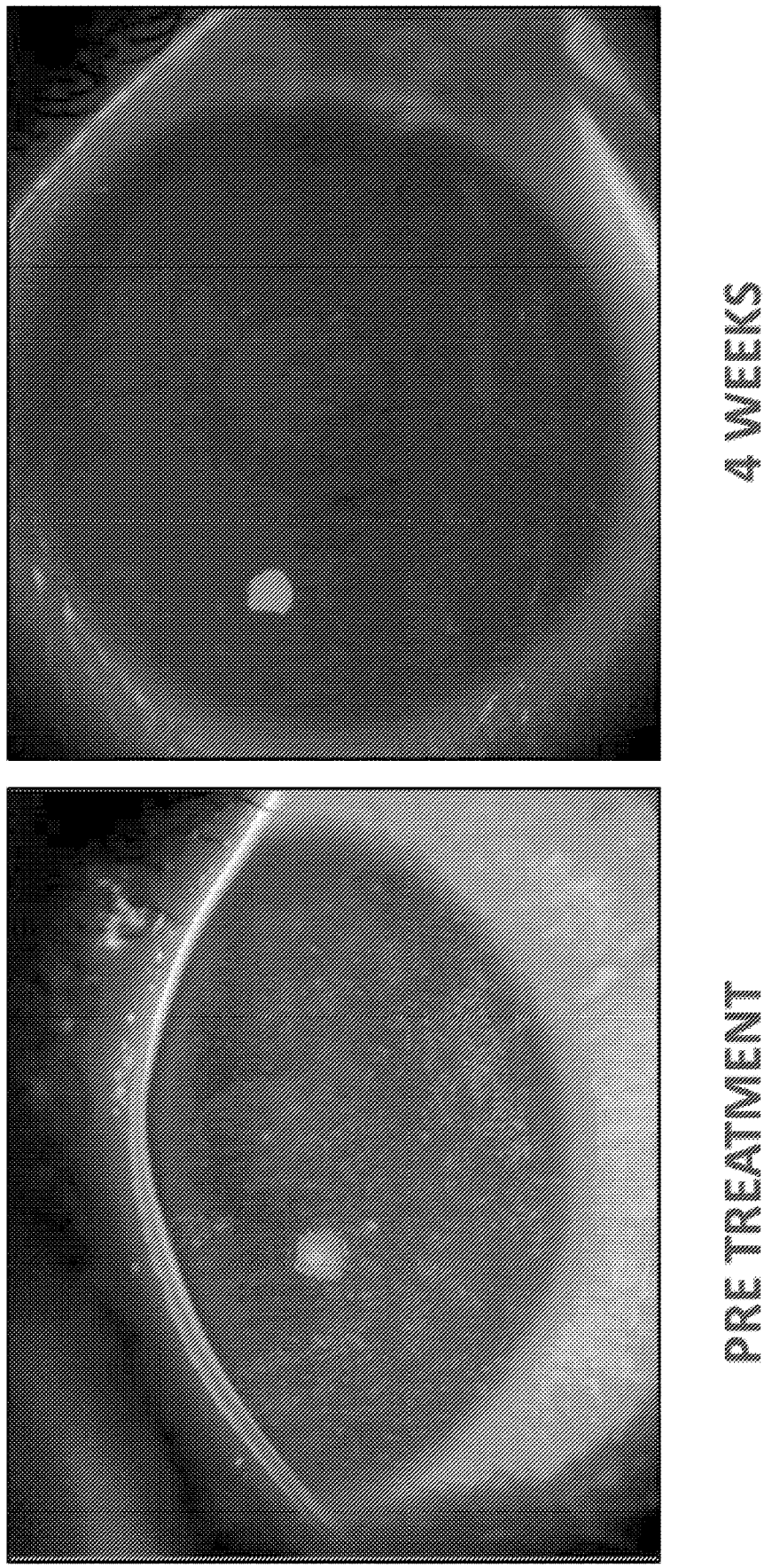
FIG. 15 shows the improvement in corneal condition demonstrated by Fluorescein staining in a pre-treated cornea and 4 weeks after treatment for an example patient, according to some embodiments.

An example of the change in corneal staining is shown in FIG. 15, which shows the improvement in corneal condition demonstrated by Fluorescein staining score improvement in a pre-treated cornea and four (4) weeks after treatment for an exemplary patient from the five patients whose staining data was shown in FIG. 14, using devices and methods as described herein.

While the invention has been described using some specific examples, many modifications and variations are possible. It is therefore understood that the invention is not intended to be limited in any way, other than by the scope of the appended claims.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the scope of the invention.

The invention claimed is:

1. A device for treating a living tissue with magnetic fields, the device comprising:
   one or more coil applicators, each having
      a face and a stimulating coil housed therein configured to face a tissue to be treated, wherein the stimulating coil includes a core and windings,
      a ferromagnetic reflector plate adjacent to the stimulating coil, the ferromagnetic reflector plate having a plane defining a rear side and a front side of the stimulating coil, the front side being configured to be oriented toward the tissue to be treated and the rear side being configured to be oriented facing away from the tissue to be treated, and
      a cooling mechanism configured to cool the stimulating coil; and
   a generator configured to drive the stimulating coil,
   wherein the device is configured to provide a magnetic field in a range of at least 0.1 T to 3 T at a distance of 1 cm or less from the face of the one or more coil applicators,
   said device having a shape in a form of eyeglasses.

2. The device of claim 1, wherein the core is a ferromagnetic core disposed within the stimulating coil and the ferromagnetic reflector plate is adjacent to the stimulating coil and to the core.

3. The device of claim 1, wherein the ferromagnetic reflector plate comprises a groove for a lead/wire that electrically connects the stimulating coil with circuitry.

4. The device of claim 1, further comprising an air flow shell with openings, the air flow shell enclosing the stimulating coil and configured to enable air to flow around the stimulating coil, and to prevent contact between the tissue and the stimulating coil.

5. The device of claim 1, wherein the cooling mechanism comprises a heat sink and at least one cooling fan.

6. The device of claim 1, wherein the generator is configured to generate magnetic pulses having an amplitude of up to about 3 T, length of 50 to 2000 μs, frequency up to 200 pulses/s, and a rate of change of at least 1000 T/s.

7. The device of claim 1, wherein the core and the ferromagnetic reflector plate are configured to form a ferromagnetic body that reflects the magnetic field, created in the stimulating coil, towards the treated tissue, thereby minimizing energy losses and cooling requirements.

8. The device of claim 1, wherein the core and the ferromagnetic reflector plate are made of reactive sintered iron.

9. The device of claim 5, wherein the heat sink comprises a flat, heat-conductive portion adjacent to the ferromagnetic reflector plate, the heat-conductive portion comprising a groove configured to reduce eddy currents.

10. The device of claim 1, further comprising an apparatus configured to fix a position of the tissue at a distance from the stimulating coil and a direction with respect to the stimulating coil.

11. The device of claim 10, wherein the distance is 10 mm or less.

12. The device of claim 1, further comprising one or more spacers configured to define a distance between the stimulating coil and the tissue to be treated.

13. The device of claim 12, wherein the one or more spacers comprise an insulating layer having a thickness of 10 mm or less.

14. The device of claim 10, wherein the apparatus comprises a resting place for a human chin and/or forehead.

15. A device for treating a living tissue with magnetic fields, the device comprising:
   one or more coil applicators, each having
      a face and a stimulating coil housed therein configured to face a tissue to be treated, wherein the stimulating coil includes a core and windings,
      a ferromagnetic reflector plate adjacent to the stimulating coil, the ferromagnetic reflector plate having a plane defining a rear side and a front side of the stimulating coil, the front side being configured to be oriented toward the tissue to be treated and the rear side being configured to be oriented facing away from the tissue to be treated, and
      a cooling mechanism configured to cool the stimulating coil, said cooling mechanism comprising a heat sink and at least one cooling fan, said heat sink comprising a flat, heat-conductive portion adjacent to the ferromagnetic reflector plate, the heat-conductive portion comprising a groove configured to reduce eddy currents; and
   a generator configured to drive the stimulating coil,
   the device being configured to provide a magnetic field in a range of at least 0.1 T to 3 T at a distance of 1 cm or less from the face of the one or more coil applicators, and
   the ferromagnetic reflector plate comprising a flat ferromagnetic reflector plate, the flat ferromagnetic plate being connected to the flat, heat-conductive portion of the heat sink in a heat-conductive interface.

16. A device for treating a living tissue with magnetic fields, the device comprising:
   one or more coil applicators, each having
      a face and a stimulating coil housed therein configured to face a tissue to be treated, wherein the stimulating coil includes a core and windings,
      a ferromagnetic reflector plate adjacent to the stimulating coil, the ferromagnetic reflector plate having a plane defining a rear side and a front side of the stimulating coil, the front side being configured to be oriented toward the tissue to be treated and the rear side being configured to be oriented facing away from the tissue to be treated, and
      a cooling mechanism configured to cool the stimulating coil;
   an apparatus configured to fix a position of the tissue to be treated at a distance from the stimulating coil and a direction with respect to the stimulating coil, the apparatus comprising a set of joints, axes and levers thereby providing the device with multiple degrees of freedom of movement and
   a generator configured to drive the stimulating coil,
   the device being configured to provide a magnetic field in a range of at least 0.1 T to 3 T at a distance of 1 cm or less from the face of the one or more coil applicators.

* * * * *